(12) United States Patent
Barnes et al.

(10) Patent No.: US 6,316,202 B1
(45) Date of Patent: Nov. 13, 2001

(54) NUCLEIC ACIDS ENCODING COLD SENSITIVE MUTANT DNA POLYMERASES

(75) Inventors: Wayne M. Barnes; Milko B. Kermekchiev, both of St. Louis, MO (US)

(73) Assignee: Washington University, St. Louis, MO (US)

(*) Notice: Subject to any disclaimer, the term of this patent is extended or adjusted under 35 U.S.C. 154(b) by 0 days.

(21) Appl. No.: 09/777,537

(22) Filed: Feb. 6, 2001

Related U.S. Application Data

(62) Division of application No. 09/587,856, filed on Jun. 6, 2000, now Pat. No. 6,214,557.

(51) Int. Cl.⁷ .............................. C12Q 1/68; C12N 9/12; C07K 1/00; C07H 21/04
(52) U.S. Cl. .............................. 435/6; 435/194; 435/199; 435/320.1; 435/252.8; 530/350; 536/23.7; 935/10; 935/24; 935/72
(58) Field of Search ............................... 435/6, 194, 199, 435/320.1, 252.8; 530/350; 536/23.7; 935/10, 24, 72

(56) References Cited

U.S. PATENT DOCUMENTS

| | | | |
|---|---|---|---|
| 4,554,101 | 11/1985 | Hopp | 530/324 |
| 4,683,195 | 7/1987 | Mullis et al. | 435/91.2 |
| 4,683,202 | 7/1987 | Mullis | 435/91.2 |
| 5,436,149 | 7/1995 | Barnes | 435/194 |
| 5,599,660 | 2/1997 | Ramanujam et al. | 435/4 |
| 5,616,494 | 4/1997 | Barnes | 435/252.3 |

OTHER PUBLICATIONS

Barnes, W.M., "The fidelity of Taq polymerase catalyzing PCR is improved by an N–terminal deletion", Gene, vol. 112, pp. 29–25 (1992).

Barnes, W.M., "PCR amplification of up to 35–kb DNA with high fidelity and high yield from λ bacteriophage templates", Proc. Natl. Acad. Sci. USA, vol. 91, pp. 2216–2220 (1994).

Caldwell, R.C., et al., "Randomization of Genes by PCR Mutagenesis", PCR Methods Applic., vol. 2, pp. 28–33 (1992).

Chou, Q., et al., "Prevention of pre–PCR mis–priming and primer dimerization improves low–copy–number amplifications", Nucleic Acids Res., vol. 20, No. 7, pp. 1717–1723 (1992).

(List continued on next page.)

*Primary Examiner*—Jeffrey Fredman
*Assistant Examiner*—Arun Chakrabarti
(74) *Attorney, Agent, or Firm*—Senniger, Powers, Leavitt & Roedel

(57) ABSTRACT

Provided are mutant DNA polymerase having at least one mutation which exhibit substantially reduced polymerase activity at 25° C. When compared to the same DNA polymerase without the at least one mutation and which exhibit normal or near-normal polymerase activity at optimum temperatures when compared to the same DNA polymerase without the at least one mutation. Also provided are amino acid sequences and nucleic acid sequences encoding such DNA polymerase, and vector plasmids and host cells suitable for the expression of these sequences. Also described herein are improved methods for performing polymerase chain reaction (PCR) amplification and other genetic manipulations and analyses using the mutant DNA polymerase of the invention.

41 Claims, 5 Drawing Sheets

OTHER PUBLICATIONS

Erlich, H.A., et al., "Recent advances in the polymerase chain reaction", Science, vol. 22, No. 5013, pp. 1643–1651 (1991).

Handyside, A.H., et al., "Pregnancies from biopsied human preimplantation embryos sexed by Y–specific DNA amplification", Nature, vol. 344, pp. 768–770 (1990).

Hebert, B., et al., "Increased PCR sensitivity by using paraffin wax as a reaction mix overlay", Molecular and Cellular Probes, vol. 7, pp. 249–252 (1993).

Higuchi, R., "Recombinant PCR", PCR Protocols: A Guide to Methods and Applications, pp. 177–183 (1990).

Horton, R.M., et al., "AmpliGrease: "Hot Start" PCR Using Petroleum Jelly", Biotechniques, vol. 16, No. 1, pp. 42–43 (1994).

Kellogg, D.E., et al., "TaqStart Antibody™: "Hot Start" PCR Facilitated by a Neutralizing Momoclonal Atibody Drected Aainst Taq DNA Plymerase", Biotechniques, vol. 16, No. 6, pp. 1134–1137 (1994).

Kumar, R., et al., "Oncogene detection at the single cell level", Oncogene, vol. 3, No. 6, pp. 647–651 (1988).

Lawyer, F.C., et al., "Isolation, Characterization, and Expression in *Escherichia coli* of the DNA Polymerase Gene from *Thermus aquaticus*", J. Biol. Chem., vol. 264, No. 11, pp. 6427–6437 (1989).

Leung, D.W., et al., "A Method for Random Mutagenesis of a defined DNA Segment Using a Modified Polymerase Chain Reaction", Technique—A Journal of Methods in Cell and Molecular Biology, vol. 1, No. 1, pp. 11–15, (1989).

McCormick, F., "The Polymerase Chain Reaction and Cancer Diagnosis", Cancer Cells, vol. 1, No. 2, pp. 56–61 (1989).

Moretti, T., et al., "Enhancement of PCR Amplification Yield and Specificity Using AmpliTaq Gold™ DNA Polymerase", BioTechniques, vol. 25, No. 4, pp. 716–722 (1998).

Nagano, K., et al., "fcsA29 Mutation is an Allele of polA Gene of *Escherichia coli*", Biosci. Biotechnol. Biochem., vol. 63, No. 2, pp. 427–429 (1999).

Sacramento, D., et al., "PCR technique as an alternative method for diagnosis and molecular epidemiology of rabies virus", Mol. Cell Probes, vol. 5, pp. 229–240 (1991).

Sagner, G., et al., "Rapid filter assay for the detection of DNA polymerase activity: direct identification of the gene for the DNA polymerase from *Thermus aquaticus*", Gene, vol. 97, pp. 119–123 (1991).

Saiki, R.K., et al., "Primer–Directed Enzymatic Amplification of DNA with a Thermostable DNA Polymerase", Science, vol. 239, No. 4839, pp. 487–491 (1988).

Scalice, E.R., et al., "Monoclonal antibodies prepared against the DNA polymerase from *Thermus aquaticus* are potent inhibitors of enzyme activity", Journal of Immun. Methods, vol. 172, pp. 147–163 (1994).

Shareky, D.J., et al., "Antibodies as Thermolabile Swithches: High Temperature Triggering for the Polymerase Chain Reaction", Bio/Technology, vol. 12, No. 5, pp. 506–509 (1994).

Wages, J.M., Jr., et al., "Clinical Performance of a Polymerase Chain Reaction Testing Algorithm for Diagnosis of HIV–1 Infection in Peripheral Blood Mononuclear Cells", J. Med. Virol., vol. 33, pp. 58–63 (1991).

Wernars, K., et al.,"Successful Approach for Detection of Low numbers of Enterotoxigenic *Escherichia coli* in Minced Meat by Using the Polymerase Chain Reaction", Appl. and Env. Microbiol., vol. 57, No. 7, pp. 1914–1919 (1991).

NUCLEIC ACIDS ENCODING COLD SENSITIVE MUTANT DNA POLYMERASES

This application is a divisional of U.S. patent application Ser. No. 09/587,856, filed Jun. 6, 2000, now U.S. Pat. 6,214,557 incorporated herein by reference.

FIELD OF THE INVENTION

The present invention is directed to thermostable DNA polymerase, and more particularly, to novel mutants of Thermus aquaticus polymerases (Taq DNA polymerase). Specifically, the invention is directed to novel cold-sensitive mutants of Taq DNA polymerases and other thermostable DNA polymerases capable of catalyzing the amplification of polynucleotides by PCR (the polymerase chain reaction) and exhibiting substantially reduced activity at temperatures in the range from room temperature (25° C.) to 42° C. When compared to the same polymerase without at least one of the mutations, while retaining near-normal enzyme activity and functionality at the normal optimum temperature for the enzyme, 65 to 72° C. The present invention is also directed to nucleic acid and amino acid sequences encoding such mutants of Taq DNA polymerases, and vector plasmids and host cells suitable for the expression of these DNA sequences. Also described herein is an improved method which provides for an automatic hot start for performing polymerase chain reaction (PCR) amplification and other genetic analyses and manipulations using the DNA polymerases of the invention.

BACKGROUND OF THE INVENTION

PCR is a rapid and simple method for specifically amplifying a target DNA sequence in an exponential manner. Saiki, et al. *Science* 239:487–4391 (1988). Briefly, the method as now commonly practiced utilizes a pair of primers that have nucleotide sequences complementary to the DNA which flanks the target sequence. The primers are mixed with a solution containing the target DNA (the template), a DNA polymerase and dNTPS for all four deoxynucleotides (adenosine (A), tyrosine (T), cytosine (C) and guanine(G)). The mix is then heated to a temperature sufficient to separate the two complementary strands of DNA. The mix is next cooled to a temperature sufficient to allow the primers to specifically anneal to sequences flanking the gene or sequence of interest. The temperature of the reaction mixture is then set to the optimum for the thermophilic DNA polymerase to allow DNA synthesis (extension) to proceed. The temperature regimen is then repeated to constitute each amplification cycle. Thus, PCR consists of multiple cycles of DNA melting, annealing and extension. Twenty replication cycles can yield up to a million-fold amplification of the target DNA sequence. In some applications a single primer sequence functions to prime at both ends of the target, but this only works efficiently if the primer is not too long in length. In some applications several pairs of primers are employed in a process commonly known as multiplex PCR.

The ability to amplify a target DNA molecule by PCR has applications in various areas of technology e.g., environmental and food microbiology (Wernars et al., *Appl. Env. Microbiol.*, 57:1914–1919 (1991); Hill and Keasler, *Int. J. Food Microbiol.*, 12:67–75 (1991)), clinical microbiology (Wages et al. *J. Med. Virol.*, 33:58–63 (1991); Sacramento et al., *Mol. Cell Probes*, 5:229–240 (1991)), oncology (Kumar and Barbacid, [Oncogene, 3:647–651 (1988); McCormick, *Cancer Cells*, 1:56–61 (1989)), genetic disease prognosis (Handyside et al., *Nature*, 344:768–770 (1990)), and blood banking and forensics (Jackson, *Transfusion*, 30:51–57 (1990)).

DNA polymerase obtained from the hot springs bacterium Thermus aguaticus (Taq DNA polymerase) has been instrumental in DNA amplification, DNA sequencing, and in related DNA primer extension techniques. The DNA and amino acid sequences described by Lawyer et al., *J. Biol. Chem.*, 264:6427 (1989), GenBank Accession No. J04639, define the gene encoding Thermus aquaticus DNA polymerase and the enzyme Thermus aquaticus DNA polymerase as those terms are used herein. The highly similar DNA polymerase (Tfl DNA polymerase) expressed by the closely related bacterium Thermus flavus is defined by the DNA and amino acid sequences described by Akhmetzjanov, A. A., and Vakhitov, V. A., *Nucleic Acids Research* 20: 5839 (1992), GenBank Accession No. X66105. These enzymes are representative of a family of DNA polymerases, also including Thermus thermophilus DNA polymerase, which are thermostable. These enzymes lack a 3'-exonuclease activity such as that which is effective for editing purposes in mesophilic DNA polymerases such as *E. coli*. DNA polymerase I, and phages T7, T3, and T4 DNA polymerases. Thermostable DNA polymerases which exhibit editing function are generally found in thermophilic archaebacteria such as Pyrococcus furiosus. Related DNA polymerases of this class are commonly known as Pfu, Pwo, Pfx, Vent, or Deep Vent.

The availability of thermostable DNA polymerases such as Taq DNA polymerase has both simplified and improved PCR. Taq DNA polymerase is stable up to 95° C. and its use in PCR has eliminated the necessity of repetitive addition of temperature sensitive polymerases after each thermal cycle. Additionally, Taq DNA polymerase can extend DNA at higher temperatures which tends to prevent the non-specific annealing of primers and thus, has improved the specificity and sensitivity of PCR.

Although significant progress has been made in PCR technology, the amplification of non-target oligonucleotides due to side-reactions, such as mispriming on non-target background DNA, RNA, and/or the primers themselves, still presents a significant problem. This is especially true in diagnostic applications where PCR is carried out in a milieu containing complex background DNA while the target DNA may be present in a single copy (Chou et al., *Nucleic Acid Res.*, 20:1717–1723 (1992)).

The temperature at which Taq DNA polymerase exhibits highest activity is in the range 62–72° C.; however, significant activity is exhibited at room temperature, approximately 25° C. to 37° C. In a normal or "cold start," the primers may prime DNA extension at non-specific sequences because the formation of only a few base pairs at the 3'-end of a primer can result in a stable priming complex. The result can be competitive or inhibitory products at the expense of the desired product. As an example of inhibitory product, structures consisting only of primer, sometimes called "primer dimers" are formed by the action of DNA polymerase on primers paired with each other, regardless of the true target template. The probability of undesirable primer-primer interactions increases with the number of primer pairs in the reaction, as with multiplex PCR. During PCR cycling, these non-specific extension products can compete with the desired target DNA.

Further, it has been determined that side reactions often occur when all reactants are mixed at ambient temperature before thermal cycling is initiated. One method for minimizing these side reactions is termed "hot start" PCR. Many PCR analyses, particularly the most demanding ones, benefit from a hot start. About 50% of all PCR reactions show improved yield and/or specificity if a hot start is employed, and in some cases a hot start is absolutely critical. These demanding PCR analyses include those which have very low copy numbers of target (such as 1 HIV genome per 10,000 cells), denatured DNA (many DNA extraction procedures include a boiling step, so that the template is single-stranded during reaction setup), or contaminated DNA e.g., DNA from soil or feces and/or DNA containing large amounts of RNA. However, current methods of achieving a hot start are tedious, expensive, and/or have other shortcomings.

Hot start PCR may be accomplished by various physical, chemical, or biochemical methods. In a physical hot start, the DNA polymerase or one or more reaction components that are essential for DNA polymerase activity is not allowed to contact the sample DNA until all the components required for the reaction are at a high temperature. The temperature must be high enough so that not even partial hybridization of the primers can occur at any locations other than the desired template location, in spite of the entire genome of the cell being available for non-specific partial hybridization of the primers. Thus, the temperature must be high enough so that base pairing of the primers cannot occur at template (or contaminating template) locations with less than perfect or near-perfect homology. This safe starting temperature is typically in the range of 50° C. to 75° C. and typically is about 10° C. hotter than the annealing temperature used in the PCR.

One physical way a hot start can be achieved is by using a wax barrier, such as the method disclosed in U.S. Pat. No. 5,599,660. See also Hebert et al., *Mol. Cell Probes*, 7:249–252 (1993); Horton et al., *Biotechniques*, 16:42–43 (1994). Using such methods, the PCR reaction is set up in two layers separated by a 1 mm thick layer of paraffin wax which melts at about 56° C. There are several methods which may be used to separate the reaction components into two solutions. For instance, all of the DNA is added, with 1×buffer but no dNTPs and no DNA polymerase enzyme, in a volume of 25 ml. One drop of melted wax is added and the tubes are all heated to 60° C. for one minute to allow the melted wax to form a sealing layer after which the tubes are cooled so the wax solidifies. Then a 25 ml mixture containing 1×buffer, all of the dNTPs, and the enzyme is added to each reaction. Finally, 1 drop of oil is added, to make 4 total layers. As the thermal cycler protocol heats the tubes to the first melting step (approximately 95° C.), the wax melts and floats to mix with the oil layer, and the two aqueous layers mix by convection as the temperature cycles.

One common variation involving the use of a wax barrier is that the reaction components are assembled with no magnesium ions so that the DNA polymerase enzyme is inactive. The magnesium ion encased in a wax bead is then (or initially) added. A problem with these wax methods, however, is that the wax hardens after each PCR cycle. This makes sample recovery extremely tedious, since the wax tends to plug the pipet tips used to remove the sample. This is true even if the samples are reheated to melt the wax. Another potential problem is cross-contamination if tweezers are used to add wax beads, since slight contact between the tweezers and the tube caps can move DNA template between samples before the PCR reactions start.

Another way to implement a hot start PCR is to use DNA polymerase which is inactivated chemically but reversibly, such as AMPLITAQ GOLD™ DNA polymerase. This enzyme preparation, distributed by PE Applied Biosystems, is distributed to users in inactivated form, but is reactivatable by heating. The required reactivation conditions, however, are extremely harsh to the template DNA: ten minutes at 95° C. and at a nominal pH of 8.3 or lower results in reactivation of some 30% of the enzyme which is enough to start the PCR. See Moretti, et al., *BioTechniques* 25: 716–722 (1998). Because this treatment depurinates DNA every thousand bases or so, this enzyme can not be used to amplify DNA more than a few kilobases in length. Accordingly, the use of this enzyme is most efficient when it is restricted to amplifying target DNA with a length of approximately 200 base pairs.

An additional way of implementing a hot start is to combine the Taq DNA polymerase enzyme with a Taq antibody before adding it to the reagent. This method employs a monoclonal, inactivating antibody raised against Taq DNA polymerase. See Scalice et al., *J. Immun. Methods*, 172: 147–163 (1994); Sharkey et al., *Bio/Technology*, 12:506–509 (1994); Kellogg et al., *Biotechniques*, 16: 1134–1137 (1994). The antibody inhibits the polymerase activity at ambient temperature but is inactivated by heat denaturation once the reaction is thermocycled, thus rendering the polymerase active. Unfortunately, the antibodies currently available for use in this method are not very efficient, and a 5 to 10-fold molar excess must be used to effect the advantages of a hot start PCR. For Klentaq-278, an amino-terminally deleted Thermus aquaticus DNA polymerase that starts with codon 279 which must be used at higher protein levels for long PCR (up to ten times more protein than Taq DNA polymerase), the levels of antibody necessary for a hot start become extremely high and the denatured antibody protein retains some inhibition for longer PCR targets. The original developer of anti-Taq antibodies (Kodak, now Johnson & Johnson) uses a triple-monoclonal antibody mixture which is more effective but is not commercially available and has not been tested in long PCR.

These methods used for hot starts require inclusion of an often expensive component (e.g., anti-Taq antibody) in the reaction mix and may place some undesirable constraints on the performance of the PCR such as a relatively short time period between when a reagent is prepared and when it must be used, or a lower efficiency of amplification. Therefore, it is usually preferable to perform physical hot starts in PCR if at all feasible.

A low tech, inexpensive option is to add the enzyme, the magnesium and/or the dNTPs to the reactions after they have heated up. Besides being tedious and prone to error, this method commonly results in contamination and cross-contamination of PCR samples as the reaction tubes must be opened in the thermal cycler while they are hot.

Some workers believe they are doing a hot start when they set up PCR reactions in tubes on ice, then add the tubes to a thermal cycler block pre-warmed to 95° C. Although some benefit arises from this method, the addition of only a few nucleotides to a primer can take place every second during the fifteen seconds or more that the tubes warm from 0° C. to 25° C. This is enough to initiate unwanted competitive PCR for reactions that require a hot start. Also, if many tubes are involved in an experiment, the tubes placed in the block first are heated for a longer time period at 95° C. compared to the tubes placed later in the heating block thus resulting in a lack of reproducibility between samples.

Thermophilic DNA polymerases are commonly believed to have minimized their mesotemperature activity during their evolution to optimize activity at around 70° C. According to this belief, it should not be possible to further decrease their room temperature activity without seriously compromising either their high temperature activity or their resistance to 95° C.

However, applicants conjectured the possibility that thermostable DNA polymerases could be mutated to a "cold-sensitive" phenotype in order to decrease polymerase activity at room temperature while not harming the activity at the normal optimum extension temperature for PCR, nor the thermostability required for the melting step of each PCR cycle. Such mutants are capable of catalyzing the PCR amplification and exhibiting substantially reduced activity at room temperature, yet near normal activity at optimum reaction temperatures when compared to DNA polymerases without the mutations. Such mutant DNA polymerases would be highly useful in providing a hot-start capability and could be prepared, distributed and used without any additional steps or protocol changes. Thus, by adopting a cold sensitive DNA polymerase, end users could have the advantages of a hot start for all of their PCR analyses, not just the analyses that are first demonstrated to be problematic with a normal room temperature start. Furthermore, "long and accurate" PCR (i.e., employing longer target lengths and with enhanced fidelity) could conveniently be provided the advantages of a hot start without tedious extra care or steps, and human STR typing and multiplex PCR will gain in reliability and efficiency. Such long and accurate PCR is described in Barnes, Proc. Natl. Acad. Sci. USA, 91:2216–2220 (1994) and in U.S. Pat. No. 5,436,149.

SUMMARY OF THE INVENTION

Among the several aspects of the invention, therefore, may be noted the provision of cold-sensitive mutant DNA polymerases which exhibit substantially reduced activity at about 25° C. to 37° C. and substantially similar polymerase activity at 62–72° C. When compared to DNA polymerases without the mutations; the provision of such mutants which are useful for PCR amplification techniques from DNA templates and from single colonies of E. coli, single-stranded (linear) amplification of DNA, cycle-sequencing, nucleic acid sequencing at elevated temperatures, DNA restriction digest filling, DNA labeling, in vivo footprinting and primer-directed mutagenesis. A further aspect of the invention is the provision of recombinant amino acid and nucleic acid sequences, vectors and host cells which provide for the expression of such mutant DNA polymerases. Yet another aspect of the invention is the provision of an improved method of performing polymerase chain amplification catalyzed by the novel DNA polymerases. It is a further aspect of the present invention to provide methods using a cold sensitive DNA polymerase for PCR amplification from DNA templates and from single colonies of E. coli, single-stranded (linear) amplification of DNA, nucleic acid sequencing, DNA restriction digest filling, DNA labeling, in vivo footprinting and primer-directed mutagenesis.

Other aspects and features will be in part apparent and in part pointed out hereinafter.

BRIEF DESCRIPTION OF THE FIGURES

These and other features, aspects, and advantages of the present invention will become better understood with regard to the following description, claims and accompanying drawings where:

DETAILED DESCRIPTION

Figure 1:
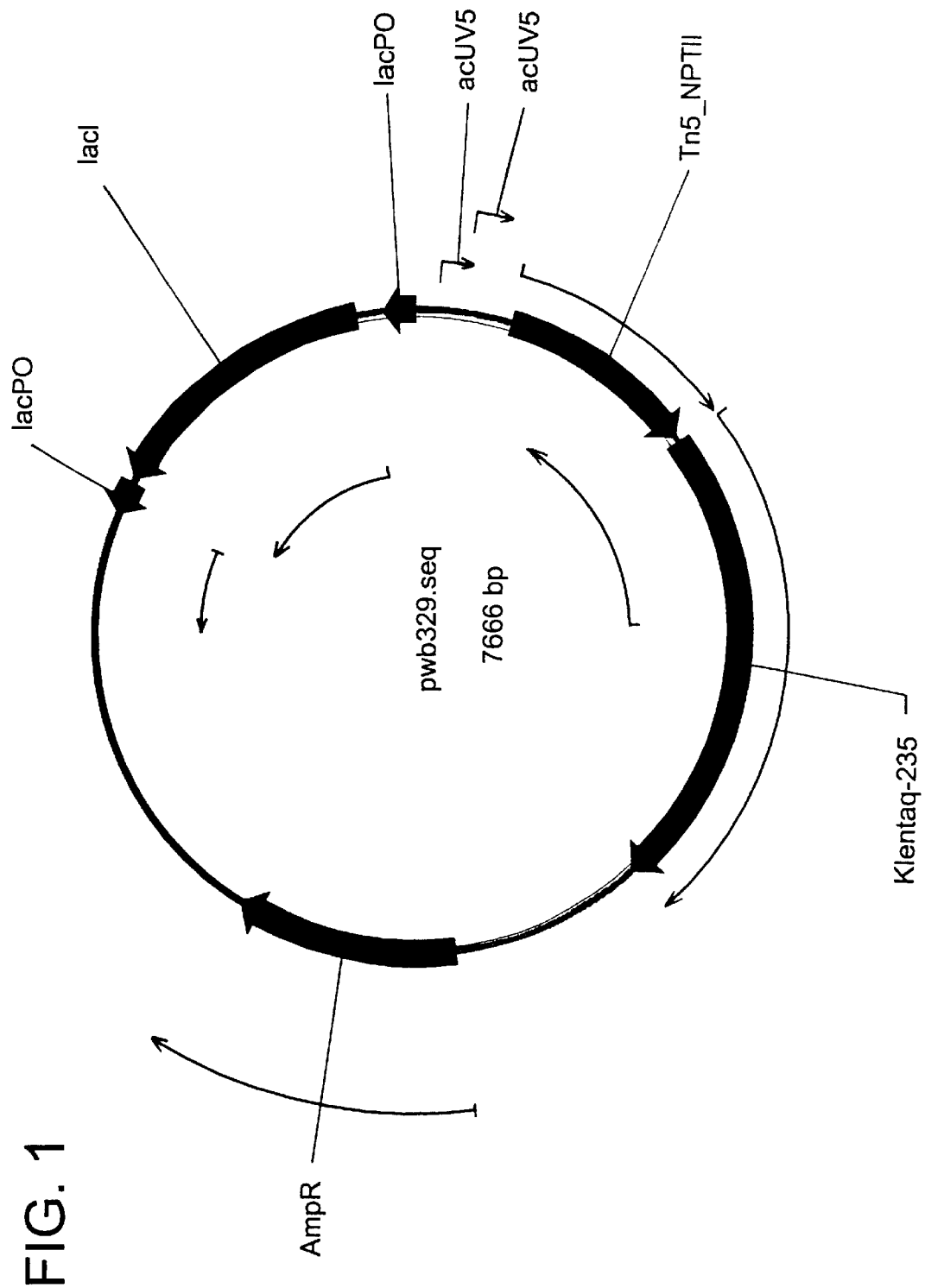
FIG. 1 is a diagram of the plasmid pWB329, which carries the wild-type sequence of Klentaq-235 as the second gene of a 2-gene operon; the first gene codes for NPTII, which kanamycin resistance. pWB329 was the template for mutagenic PCR.

All publications, patents, patent applications or other references cited in this application are herein incorporated by reference in their entirety as if each individual publication, patent, patent application or reference are specifically and individually indicated to be incorporated by reference.

Abbreviations and Definitions

The listed abbreviations and terms, as used herein, are defined as follows:

bp is the abbreviation for base pairs.

Cs is the abbreviation for cold sensitive. As used herein, a "cold sensitive" enzyme is an enzyme displaying a phenotype in which the enzyme has reduced activity at temperatures below its optimum and normal or near-normal activity at the normal optimum temperature when compared to the activity of its wild type enzyme at identical temperatures.

kb is the abbreviation for kilobase (1000 base pairs).

nt is the abbreviation for nucleotides.

ORF is the abbreviation for open reading frame.

Taq is the abbreviation for Thermus aquaticus.

Tfl is the abbreviation for Thermus flavus.

The amino acid residues are abbreviated herein according to their single letters: A represents alanine; R represents arginine; N represents asparagine; D represents aspartic acid; C represents cysteine; Q represents glutamine; E represents glutamic acid; G represents glycine; H represents histidine; I represents isoleucine; L represents leucine; K represents lysine; M represents methionine; F represents phenylalanine; P represents proline; S represents serine; T represents threonine; w represents tryptophan; Y represents tyrosine; and V represents valine.

Klentaq-nnn is an amino-terminally deleted Thermus aquaticus DNA polymerase that starts with codon nnn+1, although the start codon and the next codon may not match the wild type sequence because of alterations to the DNA sequence to produce a convenient restriction site.

Klentaq-235 is a DNA polymerase having substantially the same amino acid sequence as Thermus aquaticus DNA polymerase, but excluding the N-terminal 235 amino acids, ±one residue as claimed in U.S. Pat. No. 5,616,494, incorporated herein by reference.

Klentaq-278 is a DNA polymerase having substantially the same amino acid sequence as Thermus aquaticus DNA polymerase, but excluding the N-terminal 278 amino acids, as claimed in U.S. Pat. No. 5,436,149. The common or commercial name for this DNA polymerase is Klentaql.

WT represents wild-type (full length) or the deletion of only three amino acids, with no other known changes.

LA PCR is Long and Accurate PCR using an unbalanced mixture of two DNA polymerases, as claimed in U.S. Pat. No. 5,436,149.

ATCC is the abbreviation for American Type Culture Collection.

"Thermostable" is defined herein as having the ability to withstand temperatures up to at least 95° C. for many minutes without becoming irreversibly denatured and the ability to polymerize DNA at optimum temperatures of 55° C. to 75° C.

Processes of producing replicate copies of the same polynucleotide, such as PCR or gene cloning, are collectively referred to herein as "amplification" or "replication." For example, single or double stranded DNA may be replicated to form another DNA with the same sequence. RNA may be replicated, for example, by a RNA directed RNA polymerase, or by reverse transcribing the RNA and then performing a PCR. In the latter case, the amplified copy of the RNA is a DNA with the correlating or homologous sequence.

The polymerase chain reaction ("PCR") is a reaction in which replicate copies are made of a target polynucleotide using one or more primers, and a catalyst of polymerization, such as a DNA polymerase, and particularly a thermally stable polymerase enzyme. Generally, PCR involves repeatedly performing a "cycle" of three steps: "melting", in which the temperature is adjusted such that the DNA dissociates to single strands, "annealing", in which the temperature is adjusted such that oligonucleotide primers are permitted match their complementary base sequence using base pair recognition to form a duplex at one end of the span of polynucleotide to be amplified; and "extension" or "synthesis", which may occur at the same temperature as annealing, or in which the temperature is adjusted to a slightly higher and more optimum temperature, such that oligonucleotides that have formed a duplex are elongated with a DNA polymerase. The cycle is then repeated until the desired amount of amplified polynucleotide is obtained. Methods for PCR amplification are taught in U.S. Pat. Nos. 4,683,195 and 4,683,202.

"Hot start PCR" is a PCR method that generally produces improved reliability, improved products from low-copy targets, and/or cleaner PCR products. Template DNA and primers are mixed together and held at a temperature above the threshold of non-specific binding of primer to template. All of the PCR reaction components are added to the extension reaction except one critical reagent which is withheld. The withheld reagent is usually the thermostable polymerase or the magnesium, but it can also be, for instance, the triphosphates or the primers. Just prior to the cycling, the withheld reagent is added to allow the reaction to take place at higher temperature. Due to lack of non-specific hybridization of primers to template or to each other, the PCR amplification proceeds more efficiently as a result of the reduction or elimination of competing extensions at non-target locations. "Cold start" and "room temperature start" are used interchangeably herein and when used to refer to PCR amplification, indicate that all the PCR reaction components needed for amplification are added to the template nucleic acid sequence at 25° C.

When used to describe the temperature at which PCR amplification is conducted, "warm start" indicates that all the PCR reaction components needed for amplification are added to the template nucleic acid sequence at 30° C. or 37° C.

When referring to a particular protein such as a DNA polymerase, the term "isolated" refers to the preparation of the protein which is substantially free of contaminants.

When referring to a particular DNA polymerase, the term "polymerase activity" refers to the ability of the DNA polymerase to incorporate dNTPs or ddNTPS in a chain extension reaction. When referring to mutated DNA polymerases, the term "substantially similar DNA polymerase activity" means the mutated polymerase exhibits at least 80% of the polymerase activity of the same unmutated polymerase. When referring to mutated DNA polymerases, the term "substantially reduced DNA polymerase activity" means the mutated polymerase exhibits about 20% or less as much polymerase activity as the same unmutated polymerase.

"Reverse transcription" or "reverse transcribing" refers to the process by which RNA is converted into cDNA through the action of a nucleic acid polymerase such as reverse transcriptase. Methods for reverse transcription are well known in the art and described for example in Fredrick M. Ausubel et al. (1995), "Short Protocols in Molecular Biology," John Wiley and Sons, and Michael A. Innis et al. (1990), "PCR Protocols," Academic Press. "Stoffel fragment" refers to a DNA polymerase having substantially the same amino acid sequence as Therrnus aguaticus DNA polymerase but lacks the 5' nuclease activity due to a genetic manipulation which results in the deletion of the N-terminal 289 amino acids of the polymerase molecule. See Erlich et al., *Science* 252:1643 (1991), incorporated herein by reference. "Thermus aquaticus DNA polymerase" or "Taq DNA polymerase" are used interchangeably to refer to heat stable DNA polymerases from the bacterium Thermus aquaticus and include all Taq mutants, natural and synthesized.

The procedures disclosed herein which involve the molecular manipulation of nucleic acids are known to those skilled in the art. See generally Fredrick M. Ausubel et al. (1995), "Short Protocols in Molecular Biology," John Wiley and Sons, and Joseph Sambrook et al. (1989), "Molecular Cloning, A Laboratory Manual," second ed., Cold Spring Harbor Laboratory Press, which are both incorporated by reference.

Accordingly, the present invention is directed to novel mutant DNA polymerases which exhibit, when compared to the same unmutated DNA polymerases, substantially reduced polymerase activity at room temperature, but exhibit substantially similar polymerase activity at optimum temperature. The mutated DNA polymerases exhibit about 20% or less as much polymerase activity at 25° C. and at least about 80% or more as much polymerase activity at 68° C. when compared to the same unmutated polymerases. In a preferred embodiment, the mutated DNA polymerase exhibit about 10% or less as much polymerase activity at 25° C. and at least about 80% or more as much polymerase activity at 68° C. when compared to the same unmutated polymerase; and even more preferably, about 5% or less as much polymerase activity at 25° C. and at least 80% or more as much polymerase activity at 68° C. when compared to the same unmutated polymerase. Most preferred are those mutated DNA polymerases which exhibit about 1.5% or less as much polymerase activity at 25° C. and at least about 80% or more as much polymerase activity at 68° C. when compared to the same unmutated polymerase.

In one embodiment, the mutant DNA polymerases are thermally stable DNA polymerases. The thermostable enzyme may be obtained from various sources and may be a native or recombinant protein. Some examples of thermally stable DNA polymerases include, but are not limited to, Thermus aquaticus DNA polymerase, N-terminal deletions of Taq DNA polymerase such as Stoffel fragment DNA polymerase, Klentaq-235, and Klentaq-278; Thermus thermophilus DNA polymerase; Bacillus caldotenax DNA polymerase; Thermus flavus DNA polymerase; Bacillus stearothermophilus DNA polymerase; and archaebacterial DNA polymerases such as Thermococcus litoralis DNA polymerase (also referred to as Vent), Pfu, Pfx, Pwo, and Deep Vent. In one preferred embodiment, the mutant DNA polymerases are Thermus aquaticus polymerases, more preferably, full length or truncated Taq DNA polymerases, and even more preferably, Klentaq-235 or Klentaq-278.

It will be appreciated that minor variations incorporated into the DNA encoding for, or the amino acid sequence as described herein, which retain substantially the amino acid sequence as set forth in SEQ ID NO: 2, and which do not significantly affect the thermostability of the polymerase as included within the scope of the invention.

Those of ordinary skill in the art are aware that modifications in the amino acid sequence of a peptide, polypeptide, or protein can result in equivalent, or possibly improved, second generation peptides, etc., that display equivalent or superior functional characteristics when compared to the original amino acid sequence. The present invention accordingly encompasses such modified amino acid sequences. Alterations can include amino acid insertions, deletions, substitutions, truncations, fusions, shuffling of subunit sequences, and the like, provided that the peptide sequences produced by such modifications have substantially the same functional properties as the naturally occurring counterpart sequences disclosed herein. Thus, for example, modified cell membrane-permeant peptides should possess substantially the same transmembrane translocation and internalization properties as the naturally occurring counterpart sequence.

One factor that can be considered in making such changes is the hydropathic index of amino acids. The importance of the hydropathic amino acid index in conferring interactive biological function on a protein has been discussed by Kyte and Doolittle. See *J. Mol. Biol.*, 157:105–132, (1982). It is accepted that the relative hydropathic character of amino acids contributes to the secondary structure of the resultant protein. This, in turn, affects the interaction of the protein with molecules such as enzymes, substrates, receptors, DNA, antibodies, antigens, etc.

Based on its hydrophobicity and charge characteristics, each amino acid has been assigned a hydropathic index as follows: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate/glutamine/aspartate/asparagine (−3.5); lysine (−3.9); and arginine (−4.5).

As is known in the art, certain amino acids in a peptide or protein can be substituted for other amino acids having a similar hydropathic index or score and produce a resultant peptide or protein having similar biological activity, i.e., which still retains biological functionality. In making such changes, it is preferable that amino acids having hydropathic indices within ±2 are substituted for one another. More preferred substitutions are those wherein the amino acids have hydropathic indices within ±1. Most preferred substitutions are those wherein the amino acids have hydropathic indices within ±0.5.

Like amino acids can also be substituted on the basis of hydrophilicity. U.S. Pat. No. 4,554,101 discloses that the greatest local average hydrophilicity of a protein, as governed by the hydrophilicity of its adjacent amino acids, correlates with a biological property of the protein. The following hydrophilicity values have been assigned to amino acids: arginine/lysine (+3.0); aspartate/glutamate (+3.0 ±1); serine (+0.3); asparagine/glutamine (+0.2); glycine (0); threonine (−0.4); proline (−0.5 ±1); alanine/histidine (−0.5); cysteine (−1.0); methionine (−1.3); valine (−1.5); leucine/isoleucine (−1.8); tyrosine (−2.3); phenylalanine (−2.5); and tryptophan (−3.4). Thus, one amino acid in a peptide, polypeptide, or protein can be substituted by another amino acid having a similar hydrophilicity score and still produce a resultant protein having similar biological activity, i.e., still retaining correct biological function. In making such changes, amino acids having hydropathic indices within ±2 are preferably substituted for one another, those within ±1 are more preferred, and those within ±0.5 are most preferred.

As outlined above, amino acid substitutions in the peptides of the present invention can be based on the relative similarity of the amino acid side-chain substituents, for example, their hydrophobicity, hydrophilicity, charge, size, etc. Exemplary substitutions that take various of the foregoing characteristics into consideration in order to produce conservative amino acid changes resulting in silent changes within the present peptides, etc., can be selected from other members of the class to which the naturally occurring amino acid belongs. Amino acids can be divided into the following four groups: (1) acidic amino acids; (2) basic amino acids; (3) neutral polar amino acids; and (4) neutral non-polar amino acids. Representative amino acids within these various groups include, but are not limited to: (1) acidic (negatively charged) amino acids such as aspartic acid and glutamic acid; (2) basic (positively charged) amino acids such as arginine, histidine, and lysine; (3) neutral polar amino acids such as glycine, serine, threonine, cysteine, cystine, tyrosine, asparagine, and glutamine; and (4) neutral nonpolar amino acids such as alanine, leucine, isoleucine, valine, proline, phenylalanine, tryptophan, and methionine. It should be noted that changes which are not expected to be advantageous can also be useful if these result in the production of functional sequences.

The present invention is further directed to amino acid sequences and nucleic acid sequences encoding such mutant DNA polymerases as well as vector plasmids and host cells suitable for the expression of these DNA sequences. Preferred host cells for the expression of these DNA sequences encoding the mutant DNA polymerases are bacterial cells, insect cells, yeast, plant cells and vertebrate animal cells.

A further aspect of the invention includes the DNA polymerases encoded by the polynucleotide sequences contained in the plasmids pWB329Cs#1 and pWB329Cs#2 deposited in accordance with the Budapest Treaty on the International Recognition of the Deposit of Microorganisms for the Purpose of Patent Procedure, on Aug. 23, 1999, at American Type Culture Collection (ATCC), 10801 University Blvd., Manassas, Va. 20110–2209, USA. These strains have the designations PTA-596 and PTA-597, respectively. As mentioned herein, for clarification, ATCC Deposit No. PTA-596 is identified in the ATCC Deposit as an *E. coli* K-12 bacterial strain containing artificial plasmid pWB329Cs#1 whereas PTA-596 is more correctly described as artificial plasmid pWB302 ligated to Cs#1 as described in Examples 1–4. Similarly, ATCC Deposit No. PTA-597 is identified as an *E. coli* K-12 bacterial strain containing artificial plasmid pWB329Cs#2 whereas PTA-597 is more correctly described as artificial plasmid pWB302 ligated to Cs#2 as described in Examples 1–4.

Yet a further aspect of the invention is the DNA polymerase encoded by the polynucleotide sequence contained in plasmid pWB302Cs#3. This DNA polymerase contains three amino acid changes as indicated in Table 3 herein, at least one of which is critical to its cold-sensitive phenotype.

Uses for Mutant DNA Polymerases

The present invention provides mutant DNA polymerases which are useful for various PCR amplification techniques such as PCR amplification from DNA templates and from single colonies of *E. coli*, single-stranded (linear) amplification of DNA, nucleic acid sequencing, DNA restriction digest filling, DNA labeling, mutation detection, and primer-directed mutagenesis.

The present invention is also directed to processes for amplifying a specific nucleic acid sequence, preferably DNA or RNA, the process comprising: (a) if the nucleic acid sequence is double stranded, separating the nucleotide strands and or melting all structures in the template strands; (b) treating the single strands with oligodeoxyribonucleotide primers under conditions such that an extension product of each primer is synthesized, using a mutated DNA polymerase of the present invention which extension product is complementary to each DNA strand; and (c) separating the primer extension products from the templates on which they are synthesized to produce single stranded molecules; and (d) repeating steps b and c at least once.

The mutant DNA polymerases of the present invention can also be used to sequence nucleic acid sequences of double and single stranded PCR templates. Such method of sequencing involves producing four mixtures each consisting of nucleic acid sequence; a primer which will hybridize to the nucleic acid sequence; one labeled dNTP and three unlabeled dNTPs; the mutant DNA polymerase; and a termination nucleotide. Each of the four mixtures contains a different termination ddNTP: ddATP, ddCTP, ddGTP and ddTTP. The sequence of the nucleic acid sequence can be determined by separating the amplification products of each mixture by gel electrophoresis and visualizing the labeled DNTP by audioradiography. In one common alternative, the label is included on the ddNTPs, each with a distinctive label, and all are included in one reaction and analyzed as one electophoresis sample, instead of four separate samples.

The present invention is further directed to processes of DNA labeling using the novel mutant DNA polymerases to amplify the labeled DNA sequences. A nucleotide sequence can be labeled by providing a labeled nucleotide comprising a reporter moiety, combining the labeled nucleotide with the nucleic acid sequence template; amplifying the labeled nucleic acid sequence by polymerase chain reaction using the mutant DNA polymerases of the invention; and detecting the labeled nucleic acid sequence. The labeled nucleotide can be contained in the DNA primer. Examples of various reporter moieties are radionucleotides, fluorophores or fluorochromes, peptides, antibodies, antigens, vitamins and steroids.

The present invention is also directed to processes of in vivo footprinting using the mutant DNA polymerase to amplify the DNA. In general, analysis of the interaction of proteins with either DNA or RNA by in vivo footprinting involves first modifying the nucleic acids by the footprinting reagent in situ. Footprinting reagents are chosen based on how extensively the reactivity of a nucleic acid toward the modifying agent is altered upon interaction with the binding protein of interest. The modifications are then visualized (i.e., the analysis of the reactivity of each nucleotide of the sequence of interest) usually by PCR. See Grange et al., *Methods*, (1997) 11:151–63. Accordingly, LM-PCR is utilized to visualize modifications in DNA molecules and RL-PCR is utilized to visualize modifications in RNA molecules. Both LM-PCR and RL-PCR involve ligating a linker to the unknown 5'-ends resulting from the in vivo footprinting analysis and exponentially amplifying the region of interest. In LM-PCR, a blunt double-stranded end is created using a genespecific primer and a DNA polymerase. Then a partially doublestranded DNA linker with one blunt end is ligated to the blunt ends using a DNA ligase. The strand onto which the linker has been ligated will then serve as a template for PCR amplification. Similarly, in RL-PCR, a single stranded RNA linker is ligated to the 5' P-ends of all RNA molecules using a RNA ligase. Then a cDNA copy of the sequence of interest is synthesized using a reverse transcriptase which results in generating templates for PCR amplification. Lastly, amplified products from LM-PCR and RL-PCR are then labeled and sequenced for analysis.

The present invention is also directed to processes of primer directed mutagenesis using the mutant DNA polymerases to amplify the mutated nucleic acid sequences having substitution mutations within the target DNA sequence. The process of primer directed mutagenesis comprises contacting a nucleic acid sequence with two mutated primers, where each mutation is a mismatch when compared to the template sequence; amplifying using the novel mutated DNA polymerase; and allowing the amplified products to reanneal. The resulting nucleic acid molecules amplified using these mismatched mutated primers have mismatched bases and have a double-stranded region containing a mutant strand. See Innis et al., "PCR Protocols", Academic Press, 1990, pp 177–183.

The present invention is further directed to processes of DNA restriction digest filling using the novel mutant DNA polymerases to amplify the DNA. The mutant DNA polymerases are used in restriction digest filling to extend the 3' ends resulting from digestion with restriction enzymes for the purpose of producing 5'-sticky ends. The process comprises separating the digested DNA strands; contacting each 3' end of the separated nucleic acid molecules with oligodeoxyribonuclotide primers; extending the 3' ends using the novel mutated DNA polymerase to create blunt ends; and allowing the DNA strands with the newly synthesized 3' ends to reanneal to its complementary strand.

Construction of the Mutant Taq DNA Polymerases

The cold-sensitive DNA polymerases of the present invention are obtained by systematically mutating a thermostable DNA polymerase. In general, the production of a mutated DNA polymerase typically involves the following steps: obtaining and mutating a polynucleotide sequence encoding the DNA polymerase; providing a DNA segment comprising the mutated polynucleotides encoding a recombinant DNA polymerase; inserting the DNA segment encoding the recombinant DNA polynucleotides into an expression vector which is used to transform a host cell; and screening to identify variants having the desired characteristics.

Mutation of the polynucleotide sequence can be accomplished by a variety of methods well known in the art that are not critical to the invention. Mutation methods include, but are not limited to, chemical mutation, insertional mutation, deletion mutation, site directed mutation, random mutation, error prone PCR, oligonucleotide directed, and the like. The resulting mutated gene encodes a recombinant, thermostable DNA polymerase.

In a preferred procedure, the polynucleotide sequence encoding thermostable Thermus aguaticus DNA polymerase, preferably Klentaq-235, is mutated by subjecting the polynucleotide sequence to random mutagenesis, preferably by an "error prone" PCR technique. Error prone PCR uses low-fidelity polymerization conditions to randomly introduce a low level of point mutations within a polynucleotide sequence and may be used to mutagenize a mixture of fragments of an unknown sequence. See e.g., Leung et al., (1989) *Technique*, 1:11–15; Caldwell et al. (1992) *PCR Methods Applic.*, 2:28–33; Gram et al., (1992) *Proc. Natl. Acad. Sci.*, 89:3576–3580; Hawkins et al. (1992) *J. Mol. Biol.*, 226:889–896. The mutated polynucleotide sequences are inserted into expression vectors which are used to transform *E. coli*. The variants are then screened and those variants having the desired cold-sensitive characteristics are selected.

In general, preparation of an expression library consists of digesting the nucleotide sequences encoding a mutated DNA polymerase and a vector with site specific restriction enzymes; and ligating the vector and mutated fragment together with the resulting insertion of the mutated sequence adjacent to desired control and expression sequences. The particular vector employed will depend, in part, on the type of host cell chosen for use in gene expression. Typically, a host-compatible plasmid will be used containing genes for markers such as ampicillin or tetracycline resistance, and also containing suitable promoter and terminator sequences.

Specific nucleotide sequences in the vector are cleaved by site-specific restriction enzymes such as NcoI and HindIII. Then, after optional alkaline phosphatase treatment of the vector, the vector and target fragment are ligated together with the resulting insertion of the target codons in place adjacent to desired control and expression sequences.

The DNA vector is then typically introduced into host cells, via a procedure commonly known as transformation or transfection. Transformation of appropriate host cells may be performed using methods well known in the art. The transformed host cells are cultured under favorable conditions to effect the production of the recombinant thermostable DNA polymerase by expression of the gene and subsequent protein production in the compatible transformed host. The control sequences, expression vectors, and transformation methods are dependent on the type of host cell used to express the gene.

A host cell is transformed using a protocol designed specifically for the particular host cell. For *E. coli*, a calcium treatment, Cohen, S. N., *Proc. Natl. Acad. Sci.* 69:2110 (1972), produces the transformation. Bacteria, e.g., various strains of *E. coli*, and yeast, e.g., Baker s yeast, are frequently used as host cells for expression of DNA polymerase, although techniques for using more complex cells are known. See, e.g., procedures for using plant cells described by Depicker, A., et al., *J. Mol. Appl. Gen.* (1982) 1:561.

Alternatively and more efficiently, electroporation of salt-free *E. coli* is performed after the method of Dower et al. (1988), *Nucleic Acids Research* 16:6127–6145. After transformation, the transformed hosts are selected from other bacteria based on characteristics acquired from the expression vector, such as ampicillin resistance, and then the transformed colonies of bacteria are further screened for the ability to give rise to high levels of isopropylthiogalactoside (IPTG)-induced thermostable DNA polymerase activity. Colonies of transformed *E. coli* are then grown in large quantity and expression of the DNA polymerase is induced for isolation and purification.

The expressed thermostable DNA polymerase is then isolated using a variety of methods known in the art and screened for desired characteristics. Although a variety of purification techniques are known, all involve the steps of disruption of the *E. coli* cells, inactivation and removal of native proteins and precipitation of nucleic acids. The DNA polymerase is separated by taking advantage of such characteristics as its weight (centrifugation), size (dialysis, gel-filtration chromatography), or charge (ion-exchange chromatography). Generally, combinations of these techniques are employed together in the purification process.

The following examples are intended to illustrate but not limit the present invention.

EXAMPLES

Example 1

Construction of pWB329 pWB250 containing a NPTII gene (from transposon Tn5) was digested with HindIII. After 90 minutes of digestion with HindIII, calf intestine alkaline phosphatase (2 units per 100 l) was added to the mixture for an additional 30 minutes at 37° C. The plasmid pWB253 (see U.S. Pat. No. 5,616,494) was digested with NcoI and one unit of Klenow fragment of DNA polymerase I in the presence of 50 mM of all 4 NTPs for 30 minutes at 37° C. The pWB250 insert was then ligated into the vector pWB253 to produce pWB329 containing a kanr gene (NPTIII) upstream of the Klentaq-235 gene in pWB253. pWB329 was used as the template DNA to extend the mutagenized sequences using non-mutagenic PCR in Example 2.

Example 2

Mutagenesis of Klentaq235

Error prone PCR was conducted using Klentaq-278 as the catalyzing DNA polymerase, no proof reader, and 0.5 mM $Mn^{2+}$ in addition to 7.0 mM $Mg^{2+}$ ion in a reaction containing a PCR buffer of 250 µl of each dNTP, 50 mM Tris pH 8.55, 16 mM ammonium sulfate. Template DNA consisted of the polynucleotide sequence encoding Klentaq-235 DNA polymerase (plasmid pWB253; see U.S. Pat. No. 5,616,494) or genomic DNA from Thermus aquaticus. The PCR primers used in the mutagenesis reactions were KT85 GCAGTACCGGGAGCTCACCAAGCTGAAGA (SEQ ID NO: 7) and Klentaq32 GCG AAG CTT ACT ACT CCT TGG CGG AGA GCC AGT CC (SEQ ID NO: 8). Both KT85 and Klentaq32 span the C-terminal half Klentaq-235 (plasmid pWB253; see U.S. Pat. No. 5,616,494) thus concentrating the mutagenesis in the portion of the enzyme known to contain the catalytic functions for DNA polymerase.

The mutagenesis reactions were performed in triplicate, using three different amounts of polymerase. For 15 cycles of mutagenic PCR (designated as m15), the template utilized was 10, 20 and 30 ng of pWB253 in 100 µl volume. For 20 and 25 cycles of mutagenic PCR (designated as m20 and m25, respectively), the template utilized was 1, 2 and 3 ng of genomic DNA from Thermus aquaticus in 100 μl volume. Mutagenic PCR cycling conditions were 60 seconds at 95° C. and 7 minutes at 65° C.

The products of the mutagenesis reactions m15, m20 and m25 were then used as primers and extended utilizing a non-mutagenic high-fidelity PCR reaction using pWB329 as the template. The other primer utilized in these reactions was oligonucleotide 4468 GGA TCT CGT CGT GAC CCA TGG CGA TGC CTG CTT GCC (SEQ ID NO: 9) which spans the NcoI site in the NPTII gene.

The triplicate PCR mutagenesis reactions (m15, m20 or m25) were pooled and precipitated with PEG. Primer oligonucleotides 4468 (SEQ ID NO: 9) and 1–2 ng plasmid pWB329 were added to each entire pellet in 200 μl of PCR buffer containing 250 μM of each dNTP, 50 mM Tris pH 9.2, 16 mM ammonium sulfate, 3.5 mM $MgCl_2$, 100 μg/ml BSA. Each reaction was divided into two tubes (tubes A and B) and 20 cycles of PCR were applied under the following cycle parameters: 70 seconds at 96° C., 30 sec at 64° C., and 7 minutes at 65° C. At cycle 12 of this final PCR, 24 pmoles of primer Klentaq32 (SEQ ID NO: 8) was added to tube B of each PCR reaction for the pooled m15, m20 and m25. This addition enhanced the final yield of the target 2 kb mutagenized PCR fragment. Each PCR reaction was precipitated twice with PEG in order to remove all dNTP and primer.

This resulted in the production of the entire DNA polymerase Klentaq-235 together with a portion of the C-terminus of NPTII (kanamycin resistance). The NPTII portion enabled selection for PCR products during the cloning into expression vector pWB302 for the production of expression libraries of mutated polymerases in E. coli. Libraries were prepared from each level of mutagenesis as described in Example 3 and screened for DNA polymerase activity as described in Example 4.

Example 3
Preparation of Mutagenized Library pWB302mk

Figure 2:
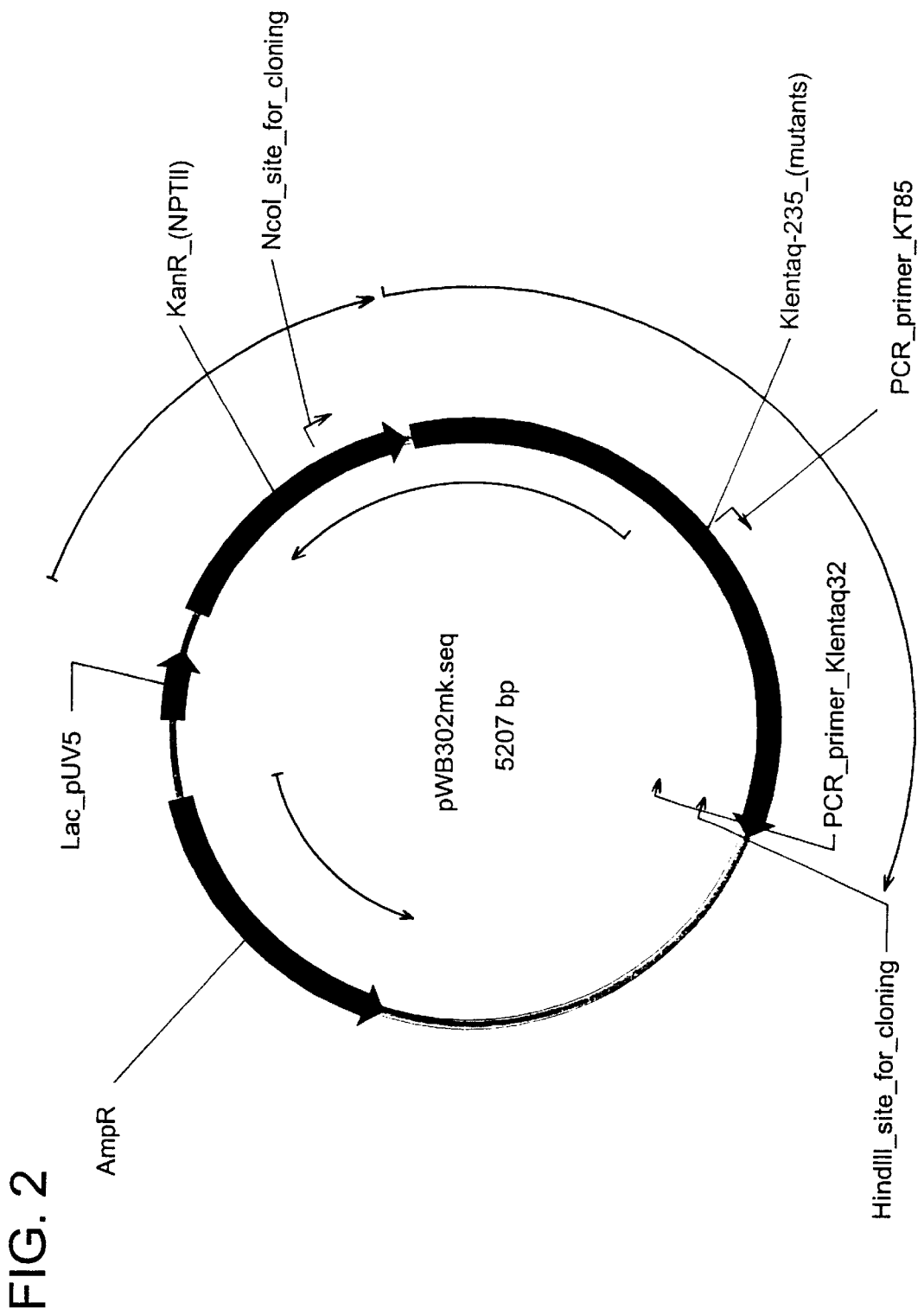
FIG. 2 is a diagram of the vector plasmid pWB302, which carries only the N-terminal portion of NPTII, and no DNA polymerase sequences at all.
Figure 3:
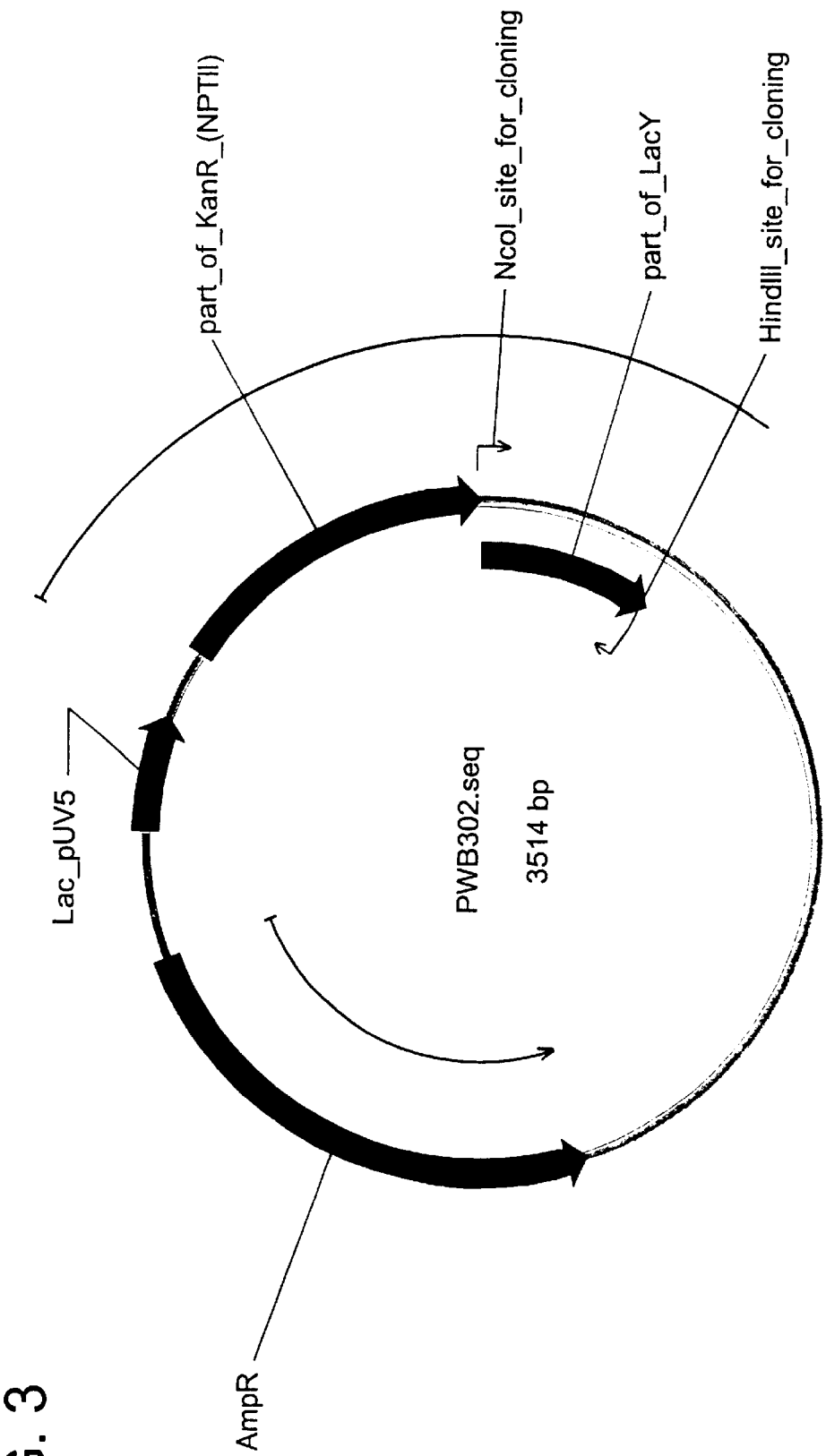
FIG. 3 is a diagram of the library plasmids pWB302mk, which are the result of cloning the PCR-mutagenized products as a library, into the suitably digested vector plasmid pWB302.

The pellets containing the mutated DNA sequences were resuspended in restriction enzyme buffer NaTMS (50 mM NaCl, 10 mM Tris pH 7.9, 10 mM $MgCl_2$, 10 mM mercaptoethanol) and digested with NcoI and HindIII for 100 minutes at 37° C. The expression vector pWB302 (FIG. 2) for cloning the mutagenized PCR product was constructed as described in Barnes, W M, Gene 112:29–35 (1992). pWB302 is essentially a deletion of pWB305 (Genbank Accession NO. M86847; Barnes 1992) between the SnaB1 and NcoI sites. pWB302 was digested with NcoI, HindIII and alkaline phosphatase. The digested target DNA and digested pWB302 were deprotonized by routine phenol extraction and ethanol precipitation and resuspended at a concentration of approximately 0.2 μg/μl. The ligase reactions contained 32.5 μl of water, 5 μl sticky-only T4 ligase buffer (40 μM rATP, 20 mM Tris pH 7.9, 5 mM $MgCl_2$, 10 mM DTT), 10 μl target DNA, 2.5 μl vector and 1 μl T4 DNA ligase. 10 μl was removed for the "before ligase" gel sample. The ligase reactions were incubated for 24 hours at 5° C. 10 μl was removed for the "after ligase" gel sample. The remaining mixture was precipitated using ethanol. The "before ligase" and "after ligase" samples were run on an agarose gel to ensure proper ligation of the mutagenesis products into pWB302.

The library of mutated DNA sequences inserted into the pWB302 vector is designated herein as pWB302mk. The region between primers KT85 (SEQ ID NO: 7) and Klentaq32 (SEQ ID NO: 8) contain the mutageneized sequences. In this system, the mutated polymerase genes are expressed at modest levels as a second gene in an artificial operon of which kanR (NPTII) is the first gene and a small portion of the kanR is included on the amplified DNA to be cloned. This provides for KanR selection so that none of the resulting library colonies is an empty vector.

Example 4
Identification of Cold Sensitive Mutants

Mutants with the desired phenotype were provisionally identified by a single-colony assay. The single-colony DNA polymerase assay used by applicants is a modification of the method of Sagner et al., Gene, 97:119–123, 1991. Using a multipin replicator apparatus, E. coli colonies containing polymerase genes mutated by the methods described above were grown under standard conditions on nitrocellulose filters at a density of up to 384 per 8×12 cm filter (microtitre plate size).

Filters containing the colonies were overlaid over a minimal volume of reaction buffer containing 50 mM Tris-HCl pH 7.9, 16 mM ammonium sulfate, 2.5 mM magnesium chloride and 0.5% Triton X-100. The filters were then heated at 68° C. for 15 minutes to inactivate endogenous E. coli DNA polymerases and any heat-sensitive mutants of Klentaq-235.

The filters were then underlaid with a minimal volume (2 ml) of reaction buffer containing 20–40 mM all four dNTPs and a microcurie of alpha-$^{32}$P-dATP, and incubated under either low temperature (37 or 42° C.) or high temperature (68° C.) conditions. To equalize the signal for comparison between the two temperatures, the low temperature samples were incubated about 4–5 times longer than the high temperature samples. In an alternative procedure, low temperature screening was conducted at 25° C. As will be apparent to those of ordinary skill in the art, when screening is conducted at 25° C., the increased incubation time needed to equalize the signals between high and low temperature conditions is increased. After incorporation, the filters were washed with 5% TCA, 1% PPi and exposed to X-Ray film or phosphoimager until the wild-type signals were easily detectable for each test temperature. Additional equalization of the low-temperature-incubation signals versus normally-high-temperature-incubation signals for unmutated control colonies was obtained by adjusting the exposure times of the final X-Ray film(s).

Colonies were selected on the basis of the difference in signal intensity generated between low and high temperature conditions. More particularly, colonies were selected that produced no detectable signal under low temperature conditions that produced full signal with wild-type, but produced a signal comparable to that generated by control, unmutated colonies under high temperature conditions. Based on these criteria, three colonies exhibiting the greatest cold sensitivity were selected and designated Cs#1, Cs#2 and Cs#3.

E. coli bacteria strains containing plasmid pWB302 ligated to Cs#1 was designated as pWB329Cs#1, and pWB302 ligated to Cs#2 was designated as pWB329Cs#2, and were deposited in accordance with the Budapest Treaty on the International Recognition of the Deposit of Microorganisms for the Purpose of Patent Procedure, on Aug. 23, 1999, at American Type Culture Collection (ATCC), 10801 University Blvd., Manassas, Va. 20110–2209, USA. These strains have the designation ATCC Deposit Nos. PTA-596 and PTA-597, respectively. For clarification, while ATCC Deposit No. PTA-596 is identified in the ATCC Deposit as E. coli K-12 with artificial plasmid pWB329Cs#1, PTA-596 is more correctly described as artificial plasmid pWB302 ligated to Cs#1 as described in Examples 1–4. Similarly, while ATCC Deposit No. PTA-597 is identified in the ATCC deposit as *E. coli* K-12 with artificial plasmid pWB329Cs#2 whereas PTA-597 is more correctly described as artificial plasmid pWB2302 ligated to Cs#2 as described in Examples 1–4.

The plasmid designated pWB329Cs#1, deposited with the ATCC as PTA-596 (plasmid pWB302 ligated to Cs#1), contains a polynucleotide sequence encoding a DNA polymerase having the mutations as indicated in Table 1. DNA sequence positions and amino acid sequence positions are numbered according to the DNA sequence and amino acid sequence of the full-length, wild-type Taq DNA polymerase as shown as SEQ ID NO: 1 and 2, respectively.

TABLE 1

Cold Sensitive Mutant DNA Polymerase #1

| DNA Change | Codon Change | Amino Acid Change |
| --- | --- | --- |
| A 1912 T | ATC to TTC | I638F |
| G 1974 T | ATG to ATA | M658I |
| T 2116 A | TGG to AGG | W706R |

The plasmid designated pWB329Cs#2, deposited with the ATCC as PTA-597 (plasmid pWB302 ligated to Cs#2), contains a polynucleotide sequence encoding a DNA polymerase having the mutations as indicated in Table 2. DNA sequence positions and amino acid sequence positions are numbered according to the DNA sequence and amino acid sequence of full-length, wild-type Taq DNA polymerase as shown as SEQ ID NO: 1 and 2, respectively.

TABLE 2

Cold Sensitive Mutant DNA Polymerase #2

| DNA Change | Codon Change | Amino Acid Change |
| --- | --- | --- |
| T 2429 G | GTG to GGG | V810G |
| A 2419 T | ATG to TTG | M807L |
| A 2042 G | GAG to GGG | E681G |
| G 2124 T | GAG to GAT | E708D | pWB302Cs#3 (plasmid pWB302mk ligated to Cs#3) contains a polynucleotide sequence encoding a DNA polymerase having the mutations as indicated in Table 3. DNA sequence positions and amino acid sequence positions are numbered according to the DNA sequence and amino acid sequence of a full-length, wild-type Taq DNA polymerase as shown as SEQ ID NO: 1 and 2, respectively.

TABLE 3

Cold Sensitive Mutant DNA Polymerase #3

| DNA Change | Codon Change | Amino Acid Change |
| --- | --- | --- |
| A 1842 T | ATA to ATT | I614I (no change) |
| G 1876 A | GAG to AAG | E626K |
| A 2069 G | CAG to CGG | Q690R |
| A 2119 C | ATT to CTT | I707L |

Using the purification procedures for Klentaq-235 and Klentaq-278 taught in U.S. Pat. Nos. 5,616,494 and 5,436,149 (as incorporated herein by reference), colonies were expanded, induced with IPTG, the cells lysed, and the mutated DNA polymerases Cs#1, Cs#2 and Cs#3 were purified.

Example 5

PCR Amplification using Cs#1 and Cs#2

To determine if the cold-sensitive DNA polymerases of the present invention provide results under room temperature start conditions similar to those achieved using conventional thermal stable polymerases and hot start conditions, Cs#1 and Cs#2 were compared to Klentaq-278 using cold start, warm start, and manual hot start conditions. The reactions were set up without magnesium in 50 ml volumes in 1×TAT buffer containing 50 mM Tris-HCl pH 9.2, 16 mM ammonium sulfate, 0.1% Tween 20. The template consisted of 5 ng of human genomic DNA. One ml (about 0.7 µg) of either Cs#1 polymerase, Cs#2 polymerase, or Klentaq-278 was used per 50 ml of reaction mix. Each 50 ml reaction also contained 250 mM of $Mg^{2+}$-free dNTPs. For the cold start and warm start conditions, magnesium chloride (to a final level of 3.5 mM) was added before a 30 minute pre-incubation at the test temperature of 25, 30 or 37° C. To create a manual hot start, the reaction pre-incubation was at 30° C. without magnesium and the magnesium chloride was added during the time period (approximately 5–7 minutes) that all the reactions were being incubated at 68° C. before the first PCR cycle. Then, cycling conditions consisted of 45 cycles of 92° C. for 40 seconds, 67° C. for 30 seconds and 68° C. for 2 minutes.

Two target sequences of differing sizes were amplified. The human tyrosine hydroxylase gene (TH01) sequence consisting of 250 bp and the human chemokine receptor 5 (CCR5) sequence consisting of 513 bp were amplified. The primer sets used are as follows:

TH01-1:

GTGGGCTGAAAAGCTCCCGATTAT (SEQ ID NO: 3)

TH01-2:

ATTCAAAGGGTATCTGGGCTCTGG (SEQ ID NO: 4)

CCR5-D5:

AGGTACCTGGCTGTCGTCCATGCTGTGTTT (SEQ ID NO: 5)

CCR5-D3:

GATGATGGGGTTGATGCAGCAGTGCGTCAT (SEQ ID NO: 6)

More particularly, for cold start PCR, 5 ml of 35 mM $MgCl_2$ were added to 45 ml of reaction mix and pre-incubated at room temperature (approximately 25° C.) for 30 minutes. For warm start PCR, the procedure was identical to that used for room temperature start except that the 30 minute pre-incubation was carried out at 30° C. For hot start PCR, the 45 ml reaction mixes were preincubated without $Mg^{++}$ at 30°0 C. for 30 minutes. Then 2–4 minutes into the initial 5–7 minute warm-up (68° C.), 5 ml of 35 mM $MgCl_2$ was added to each reaction mix. After cycling, the resulting amplification products were isolated using standard procedures well known to those of ordinary skill in the art. See, e.g., Innis et al. (1990) "PCR Protocols, A Guide to Methods and Applications," Academic Press, Inc, incorporated herein by reference.

Figure 4:
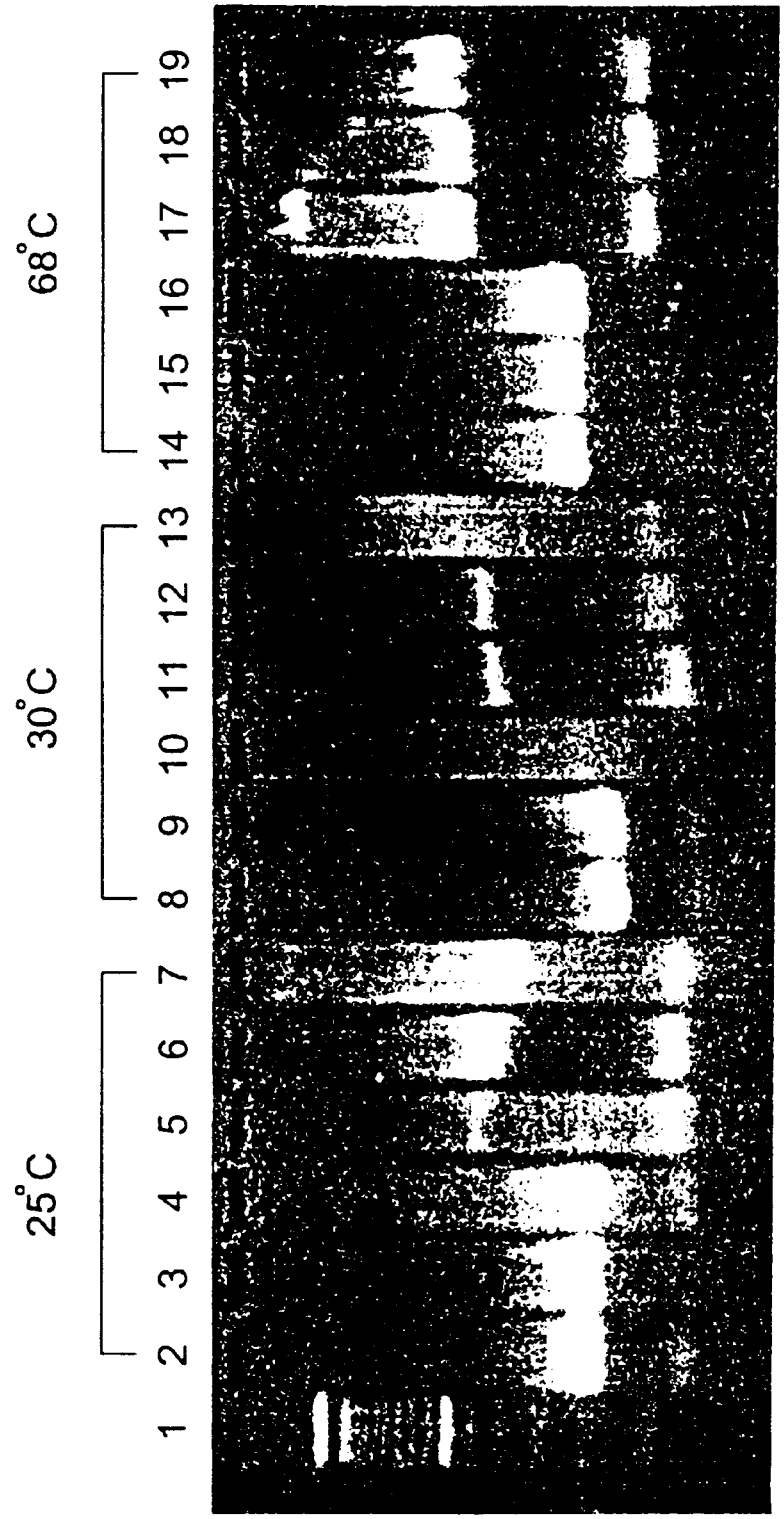
FIG. 4 is a photograph of an agarose gel depicting the amplification products obtained from a PCR amplification reaction using normal and two cold sensitive mutant DNA polymerases (Cs#1 and Cs#2) of the present invention. It should be noted that for this PCR reaction, normal polymerase Klentaq-278 does not function well under cold start and warm start conditions, but a manual hot start allows it to function. Conditions for conducting the PCR reaction are given herein.

Amplification products were visualized by agarose gel electrophoresis and ethidium bromide staining. Fifteen to eighteen ml of the amplification products were loaded into each well of the 1.4% agarose gel as shown in FIG. 4. The wells of the agarose gel contain amplification products obtained under the conditions as shown in Table 4. A 100 bp molecular weight ladder was loaded into well 1. Electrophoresis was carried out until the tracking dye had moved 5–7 cm.

TABLE 4

| Lane | PCR start conditions | Enzyme | Target DNA |
| --- | --- | --- | --- |
| 2 | cold start (25° C.) | Cs#1 | THO1 |
| 3 | cold start (25° C.) | Cs#2 | THO1 |
| 4 | cold start (25° C.) | Klentaq-278 | THO1 |
| 5 | cold start (25° C.) | Cs#1 | CCR5 |
| 6 | cold start (25° C.) | Cs#2 | CCR5 |
| 7 | cold start (25° C.) | Klentaq-278 | CCR5 |
| 8 | warm start (30° C.) | Cs#1 | THO1 |
| 9 | warm start (30° C.) | Cs#2 | THO1 |
| 10 | warm start (30° C.) | Klentaq-278 | THO1 |
| 11 | warm start (30° C.) | Cs#1 | CCR5 |
| 12 | warm start (30° C.) | Cs#2 | CCR5 |
| 13 | warm start (30° C.) | Klentaq-278 | CCR5 |
| 14 | hot start (68° C.) | Cs#1 | THO1 |
| 15 | hot start (68° C.) | Cs#2 | THO1 |
| 16 | hot start (68° C.) | Klentaq-278 | THO1 |
| 17 | hot start (68° C.) | Cs#1 | CCR5 |
| 18 | 68° C. | Cs#2 | CCR5 |
| 19 | 68° C. | Klentaq-278 | CCR5 |

As can be seen in FIG. 4, two of the cold-sensitive polymerases of the present invention, Cs#1 and Cs#2, produced sharp bands under either cold start (Cs#1 in lanes 2 and 5; Cs#2 in lanes 3 and 6), warm start (Cs#1 in lanes 8 and 11; Cs#2 in lanes 9 and 12), or hot start (Cs#1 in lanes 14 and 17; Cs#2 in lanes 15 and 18) conditions. In contrast, the use of standard Klentaq-278 resulted in the formation of sharp bands only when manual hot start conditions are utilized (lane 16 and 19). For unknown reasons, the efficiency of amplification of the larger CCR5 target sequence using the cold-sensitive polymerases under both room temperature and warm start conditions was lower than that observed for THO1. Even at this lower efficiency, the results obtained using the cold-sensitive polymerases of the present invention are superior to those obtained with Klentaq-278.

Example 6

PCR Amplification Using Cs#3

To determine whether the Cs#3 mutant polymerase of the present invention provides results under cold start conditions similar to those achieved using conventional thermal stable polymerases and hot start conditions, Cs#3 polymerase was compared to Klentaq-278 using cold start and manual hot start conditions. The target human chemokine receptor 5 (CCR5) consisting of 513 bp was amplified. PCR was carried out using CCR5-D5 (SEQ ID NO: 5) and CCR5-D3 (SEQ ID NO: 6) as primers for 35 cycles, using equal amounts (80 ng per 100 ul) of Klentaq-278 or Cs#3 polymerase. All reactions contained 1.3 M betaine and $Mg^{++}$-free dNTPs.

To create a manual hot-start, PCR samples were pre-incubated at 30° C. for 30 minutes and prior to amplification, the reactions were warmed up at 68° C. for 10 minutes. Reactions 3 and 4 were pre-incubated at 30° C. without magnesium in 45 ml volumes of 1.11×TAT buffer (1×=50 mM Tris-HCl pH 9.2, 16 mM ammonium sulfate, 0.1% Tween 20) at 30° C. for 30 minutes. Then 5 ml of 35 mM $MgCl_2$ was added to each reaction mix during the time period that all the reactions were being incubated at 68° C. before the first PCR cycle, usually 2–4 minutes into the initial 5–7 minute warm-up (68° C.). For cold start PCR, 5 ml of 35 mM were added to the reaction mix and pre-incubated at room temperature (approximately 25° C.) for 30 minutes. Amplification was conducted using the following cycling conditions for both hot start and cold start: 45 cycles at 92° C. for 40 seconds, 67° C. for 30 seconds and 68° C. for 2 minutes.

After cycling, the resulting amplification products were isolated using standard procedures well known to those of ordinary skill in the art. See, e.g., Innis et al. (1990) "PCR Protocols, A Guide to Methods and Applications," Academic Press, Inc.

Figure 5:
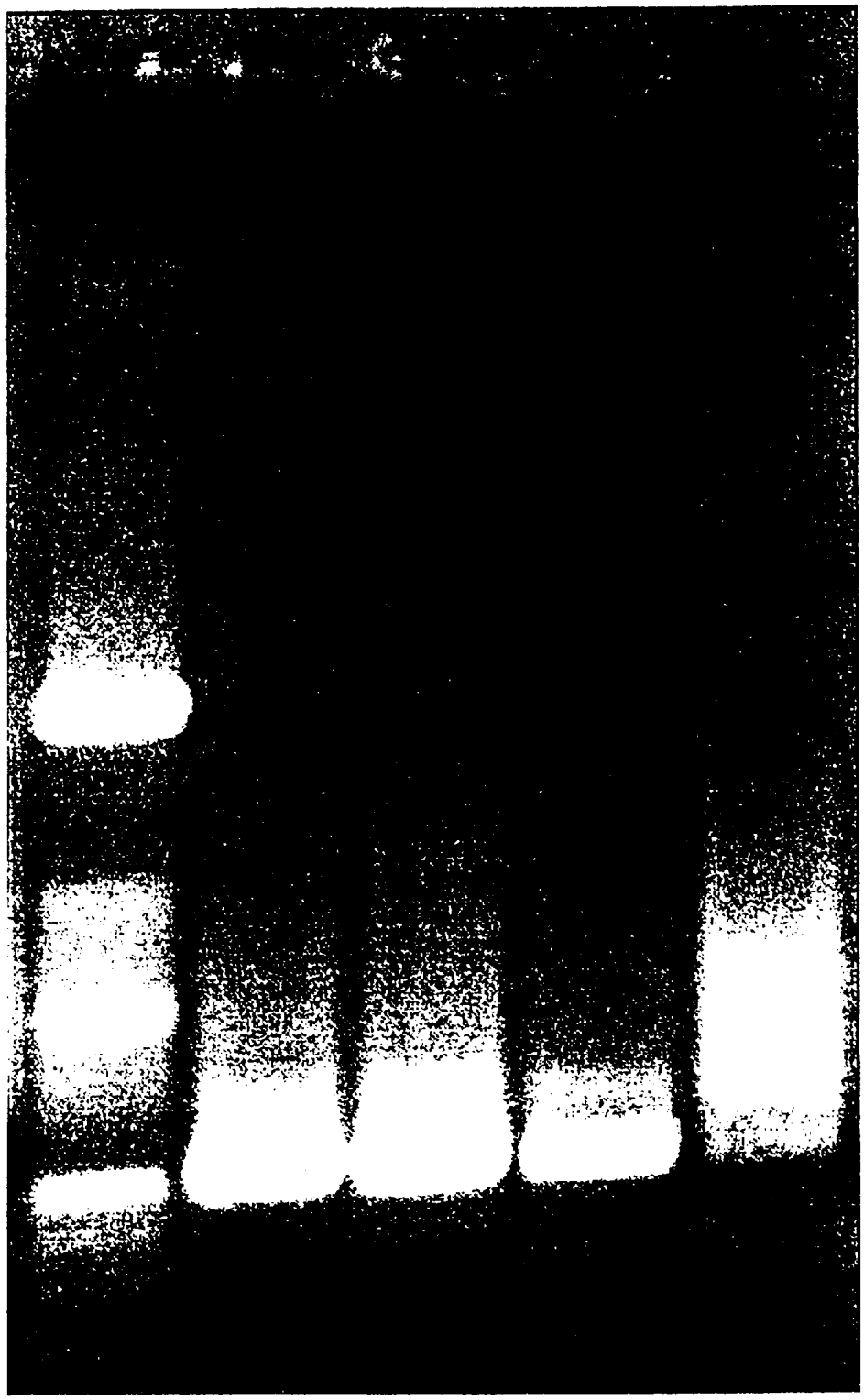
FIG. 5 is a photograph of an agarose cell depicting the amplification products obtained from a PCR amplification reaction using normal (lanes 3 and 5) and a cold sensitive mutant DNA polymerase (Cs#3) (lanes 2 and 4) of the present invention. Lane 1 contains a molecular weight standard ladder. The PCR reactions in lanes 2 and 3 were performed by a manual hot start method and the PCR reactions in lanes 4 and 5 were conducted at room temperature (25° C.) and demonstrate the functional advantage of the mutant DNA polymerases of the present invention. Conditions for conducting the PCR reaction are given herein.

Amplified CCR5 products were visualized by agarose gel electrophoresis and ethidium bromide staining. Fifteen to eighteen ml of amplified CCR5 products were loaded into wells 1–4 of an 1.4% agarose gel as shown in FIG. 5. The wells of the agarose gel contain amplification products obtained under the conditions as shown in Table 5. A 100 bp molecular weight ladder was loaded into well 1. Electrophoresis was carried out until the tracking dye had moved 5–7 cm.

TABLE 5

| Lane | PCR Start Conditions | Enzyme | Target DNA |
| --- | --- | --- | --- |
| 2 | hot start (68° C.) | Cs#3 | CCRD5 |
| 3 | cold start (25° C.) | Cs#3 | CCRD5 |
| 4 | cold start (25° C.) | Klentaq-278 | CCRD5 |

As can be seen in FIG. 5, use of the Cs#3 polymerase produced sharp bands under either cold start (lane 4) or hot start (lane 2) conditions. In contrast, the use of standard Klentaq-278 resulted in the formation of sharp bands only when manual hot start (lane 3) conditions were utilized. These results clearly demonstrate that the use of the cold-sensitive polymerases of the present invention eliminate the side reactions observed with conventional thermal stable polymerases, thus providing the advantages observed with hot start PCR without the potential error and contamination problems currently associated with hot start PCR.

In light of the detailed description of the invention and the examples presented above, it can be appreciated that the several aspects of the invention are achieved.

It is to be understood that the present invention has been described in detail by way of illustration and example in order to acquaint others skilled in the art with the invention, its principles, and its practical application. Further, the specific embodiments of the present invention as set forth are not intended as being exhaustive or limiting of the invention, and that many alternatives, modifications, and variations will be apparent to those skilled in the art in light of the foregoing examples and detailed description. Accordingly, this invention is intended to embrace all such alternatives, modifications, and variations that fall within the spirit and scope of the following claims. While some of the examples and descriptions above include some conclusions about the way the invention may function, the inventors do not intend to be bound by those conclusions and functions, but puts them forth only as possible explanations.

We claim:

1. A polynucleotide comprising a nucleotide sequence encoding a mutant DNA polymerase comprising at least one mutation, said mutant DNA polymerase exhibiting substantially reduced polymerase activity when compared to the same polymerase without the at least one mutation at 25° C. and substantially similar polymerase activity when compared to the same polymerase without the at least one mutation at 68° C., said polynucleotide contained in the plasmid pWB302mk present in the host cell selected from the group consisting of: ATCC Deposit Nos. PTA-596 and PTA-597.

2. The polynucleotide of claim 1 wherein the at least one mutation is selected from the group consisting of (1) an A to T substitution at position 1912 of the nucleic acid sequence depicted in SEQ ID NO: 1; (2) a G to T substitution at position 1974 of the nucleic acid sequence depicted in SEQ ID NO: 1; and (3) a T to A substitution at position 2116 of the nucleic acid sequence depicted in SEQ ID NO: 1.

3. A DNA vector comprising the polynucleotide of claim 2.

4. A host cell comprising the vector of claim 3.

5. The polynucleotide of claim 1 wherein the at least one mutation is selected from the group consisting of (1) a T to G substitution at position 2429 of the nucleic acid sequence depicted in SEQ ID NO: 1; (2) an A to T substitution at position 2419 of the nucleic acid sequence depicted in SEQ ID NO: 1; (3) an A to G substitution at position 2042 of the nucleic acid sequence depicted in SEQ ID NO: 1; and (4) a G to T substitution at position 2124 of the nucleic acid sequence depicted in SEQ ID NO: 1.

6. A DNA vector comprising the polynucleotide of claim 5.

7. A host cell comprising the vector of claim 6.

8. A polynucleotide comprising a nucleotide sequence encoding a mutant DNA polymerase comprising at least one mutation, said mutant DNA polymerase exhibiting substantially reduced polymerase activity when compared to the same polymerase without the at least one mutation at 25° C. and substantially similar polymerase activity when compared to the same polymerase without the at least one mutation at 68° C., wherein the at least one mutation is selected from the group consisting of (1) an A to T substitution at position 1912 of the nucleic acid sequence depicted in SEQ ID NO: 1; (2) a G to T substitution at position 1974 of the nucleic acid sequence depicted in SEQ ID NO: 1; and (3) a T to A substitution at position 2116 of the nucleic acid sequence depicted in SEQ ID NO: 1.

9. A polynucleotide comprising a nucleotide sequence encoding a mutant DNA polymerase comprising at least one mutation, said mutant DNA polymerase exhibiting substantially reduced polymerase activity when compared to the same polymerase without the at least one mutation at 25° C. and substantially similar polymerase activity when compared to the same polymerase without the at least one mutation at 68° C., wherein the at least one mutation is selected from the group consisting of (1) a T to G substitution at position 2429 of the nucleic acid sequence depicted in SEQ ID NO: 1; (2) an A to T substitution at position 2419 of the nucleic acid sequence depicted in SEQ ID NO: 1; (3) an A to G substitution at position 2042 of the nucleic acid sequence depicted in SEQ ID NO: 1; and (4) a G to T substitution at position 2124 of the nucleic acid sequence depicted in SEQ ID NO: 1.

10. A polynucleotide comprising a nucleotide sequence encoding a mutant DNA polymerase comprising at least one mutation, said mutant DNA polymerase exhibiting substantially reduced polymerase activity when compared to the same polymerase without the at least one mutation at 25° C. and substantially similar polymerase activity when compared to the same polymerase without the at least one mutation at 68° C., wherein the at least one mutation is selected from the group consisting of (1) an A to T substitution at position 1842 of the nucleic acid sequence depicted in SEQ ID NO: 1; (2) a G to A substitution at position 1876 of the nucleic acid sequence depicted in SEQ ID NO: 1; (3) an A to G substitution at position 2069 of the nucleic acid sequence depicted in SEQ ID NO: 1; and (4) an A to C substitution at position 2119 of the nucleic acid sequence depicted in SEQ ID NO: 1.

11. A DNA vector comprising the polynucleotide of claim 10.

12. A host cell comprising the vector of claim 11.

13. A recombinant plasmid comprising plasmid pWB302mk containing a mutant DNA polymerase comprising at least one mutation, said mutant DNA polymerase exhibiting substantially reduced polymerase activity when compared to the same polymerase without the at least one mutation at 25° C. and substantially similar polymerase activity when compared to the same polymerase without the at least one mutation at 68° C.

14. The polynucleotide of claim 1 wherein said mutant DNA polymerase exhibits about 20% or less as much polymerase activity when compared to the same polymerase without the at least one mutation at 25° C. and at least about 80% or more as much polymerase activity when compared to the same polymerase without the at least one mutation at 68° C.

15. The polynucleotide of claim 14 wherein the mutant DNA polymerase exhibits about 10% or less as much polymerase activity when compared to the same polymerase without the at least one mutation at 25° C. and at least about 80% or more as much polymerase activity when compared to the same polymerase without the at least one mutation at 68° C.

16. The polynucleotide of claim 15 wherein the mutant DNA polymerase exhibits about 5% or less as much polymerase activity when compared to the same polymerase without the at least one mutation at 25° C. and at least about 80% or more as much polymerase activity when compared to the same polymerase without the at least one mutation at 68° C.

17. The polynucleotide of claim 16 wherein the mutant DNA polymerase exhibits at least about 1.5% or less as much polymerase activity when compared to the same polymerase without the at least one mutation at 25° C. and at least about 80% or more as much polymerase activity when compared to the same polymerase without the at least one mutation at 68° C.

18. The polynucleotide of claim 1 wherein the polymerase is a thermostable polymerase.

19. The polynucleotide of claim 18 wherein the thermostable DNA polymerase is a full length or truncated Taq polymerase.

20. The polynucleotide of claim 18 wherein the thermostable DNA polymerase is selected from the group consisting of *Thermus aquaticus* DNA polymerase; N-terminal deletions of Taq DNA polymerase comprising a Stoffel fragment DNA polymerase, Klentaq-235, and Klentaq-278; *Thermus thermophilus* DNA polymerase; *Bacillus caldotenax* DNA polymerase; *Thermus flavus* DNA polymerase; *Bacillus stearothermophilus* DNA polymerase; and archaebacterial DNA polymerases comprising *Thermococcus litoralis* DNA polymerase, Pfu, Pfx, Pwo, and Deep Vent.

21. The polynucleotide of claim 2 wherein said mutant DNA polymerase exhibits about 20% or less as much polymerase activity when compared to the same polymerase without the at least one mutation at 25° C. and at least about 80% or more as much polymerase activity when compared to the same polymerase without the at least one mutation at 68° C.

22. The polynucleotide of claim 21 wherein the mutant DNA polymerase exhibits about 10% or less as much polymerase activity when compared to the same polymerase without the at least one mutation at 25° C. and at least about 80% or more as much polymerase activity when compared to the same polymerase without the at least one mutation at 68° C.

23. The polynucleotide of claim 22 wherein the mutant DNA polymerase exhibits about 5% or less as much polymerase activity when compared to the same polymerase without the at least one mutation at 25° C. and at least about 80% or more as much polymerase activity when compared to the same polymerase without the at least one mutation at 68° C.

24. The polynucleotide of claim 23 wherein the mutant DNA polymerase exhibits at least about 1.5% or less as much polymerase activity when compared to the same polymerase without the at least one mutation at 25° C. and at least about 80% or more as much polymerase activity when compared to the same polymerase without the at least one mutation at 68° C.

25. The polynucleotide of claim 5 wherein said mutant DNA polymerase exhibits about 20% or less as much polymerase activity when compared to the same polymerase without the at least one mutation at 25° C. and at least about 80% or more as much polymerase activity when compared to the same polymerase without the at least one mutation at 68° C.

26. The polynucleotide of claim 25 wherein the mutant DNA polymerase exhibits about 10% or less as much polymerase activity when compared to the same polymerase without the at least one mutation at 25° C. and at least about 80% or more as much polymerase activity when compared to the same polymerase without the at least one mutation at 68° C.

27. The polynucleotide of claim 26 wherein the mutant DNA polymerase exhibits about 5% or less as much polymerase activity when compared to the same polymerase without the at least one mutation at 25° C. and at least about 80% or more as much polymerase activity when compared to the same polymerase without the at least one mutation at 68° C.

28. The polynucleotide of claim 27 wherein the mutant DNA polymerase exhibits at least about 1.5% or less as much polymerase activity when compared to the same polymerase without the at least one mutation at 25° C. and at least about 80% or more as much polymerase activity when compared to the same polymerase without the at least one mutation at 68° C.

29. The polynucleotide of claim 8 wherein said mutant DNA polymerase exhibits about 20% or less as much polymerase activity when compared to the same polymerase without the at least one mutation at 25° C. and at least about 80% or more as much polymerase activity when compared to the same polymerase without the at least one mutation at 68° C.

30. The polynucleotide of claim 29 wherein the mutant DNA polymerase exhibits about 10% or less as much polymerase activity when compared to the same polymerase without the at least one mutation at 25° C. and at least about 80% or more as much polymerase activity when compared to the same polymerase without the at least one mutation at 68° C.

31. The polynucleotide of claim 30 wherein the mutant DNA polymerase exhibits about 5% or less as much polymerase activity when compared to the same polymerase without the at least one mutation at 25° C. and at least about 80% or more as much polymerase activity when compared to the same polymerase without the at least one mutation at 68° C.

32. The polynucleotide of claim 31 wherein the mutant DNA polymerase exhibits at least about 1.5% or less as much polymerase activity when compared to the same polymerase without the at least one mutation at 25° C. and at least about 80% or more as much polymerase activity when compared to the same polymerase without the at least one mutation at 68° C.

33. The polynucleotide of claim 9 wherein said mutant DNA polymerase exhibits about 20% or less as much polymerase activity when compared to the same polymerase without the at least one mutation at 25° C. and at least about 80% or more as much polymerase activity when compared to the same polymerase without the at least one mutation at 68° C.

34. The polynucleotide of claim 33 wherein the mutant DNA polymerase exhibits about 10% or less as much polymerase activity when compared to the same polymerase without the at least one mutation at 25° C. and at least about 80% or more as much polymerase activity when compared to the same polymerase without the at least one mutation at 68° C.

35. The polynucleotide of claim 34 wherein the mutant DNA polymerase exhibits about 5% or less as much polymerase activity when compared to the same polymerase without the at least one mutation at 25° C. and at least about 80% or more as much polymerase activity when compared to the same polymerase without the at least one mutation at 68° C.

36. The polynucleotide of claim 35 wherein the mutant DNA polymerase exhibits at least about 1.5% or less as much polymerase activity when compared to the same polymerase without the at least one mutation at 25° C. and at least about 80% or more as much polymerase activity when compared to the same polymerase without the at least one mutation at 68° C.

37. The polynucleotide of claim 10 wherein said mutant DNA polymerase exhibits about 20% or less as much polymerase activity when compared to the same polymerase without the at least one mutation at 25° C. and at least about 80% or more as much polymerase activity when compared to the same polymerase without the at least one mutation at 68° C.

38. The polynucleotide of claim 37 wherein the mutant DNA polymerase exhibits about 10% or less as much polymerase activity when compared to the same polymerase without the at least one mutation at 25° C. and at least about 80% or more as much polymerase activity when compared to the same polymerase without the at least one mutation at 68° C.

39. The polynucleotide of claim 38 wherein the mutant DNA polymerase exhibits about 5% or less as much polymerase activity when compared to the same polymerase without the at least one mutation at 25° C. and at least about 80% or more as much polymerase activity when compared to the same polymerase without the at least one mutation at 68° C.

40. The polynucleotide of claim 39 wherein the mutant DNA polymerase exhibits at least about 1.5% or less as much polymerase activity when compared to the same polymerase without the at least one mutation at 25° C. and at least about 80% or more as much polymerase activity when compared to the same polymerase without the at least one mutation at 68° C.

41. A host cell comprising the plasmid of claim 13.

* * * * *

SEQUENCE LISTING

<160> NUMBER OF SEQ ID NOS: 9

<210> SEQ ID NO 1
<211> LENGTH: 2499
<212> TYPE: DNA
<213> ORGANISM: Thermus aquaticus

<400> SEQUENCE: 1

| | | | | | |
|---|---|---|---|---|---|
| atgaggggga | tgctgccct | ctttgagccc | aagggccggg | tcctcctggt | ggacggccac | 60 |
| cacctggcct | accgcacctt | ccacgccctg | aagggcctca | ccaccagccg | ggggagccg | 120 |
| gtgcaggcgg | tctacggctt | cgccaagagc | ctcctcaagg | ccctcaagga | ggacgggga | 180 |
| gcggtgatcg | tggtctttga | cgccaaggcc | cctccttcc | gccacgaggc | ctacggggg | 240 |
| tacaaggcgg | ccgggcccc | cacgccgag | gactttcccc | ggcaactcgc | cctcatcaag | 300 |
| gagctggtgg | acctcctggg | gctggcgcgc | ctcgaggtcc | cgggctacga | ggcggacgac | 360 |
| gtcctggcca | gctggccaa | gaaggcgaa | aaggagggct | acgaggtccg | catcctcacc | 420 |
| gccgacaaag | acctttacca | gctcctttcc | gaccgcatcc | acgtcctcca | ccccgagggg | 480 |
| tacctcatca | ccccggcctg | gctttgggaa | agtacggcc | tgaggcccga | ccagtgggcc | 540 |
| gactaccggg | ccctgaccgg | ggacgagtcc | gacaaccttc | cgggtcaa | ggcatcggg | 600 |
| gagaagacgg | cgaggaagct | tctggaggag | tggggagcc | tggaagccct | cctcaagaac | 660 |
| ctggaccggc | tgaagcccgc | catccggag | aagatcctgg | cccacatgga | cgatctgaag | 720 |
| ctctcctggg | acctgccaa | ggtgcgcacc | gacctgcccc | tggaggtgga | cttcgccaaa | 780 |
| aggcgggagc | ccgaccggga | gaggcttagg | gcctttctgg | agaggcttga | gttggcagc | 840 |
| ctcctccacg | agttcggcct | tctggaaagc | cccaaggccc | tggaggaggc | ccctggccc | 900 |
| ccgccggaag | ggccttcgt | gggctttgtg | ctttccgca | aggagcccat | gtgggccgat | 960 |
| cttctggccc | tggccgccgc | caggggggc | cgggtccacc | gggcccccga | gccttataaa | 1020 |
| gccctcaggg | acctgaagga | ggcgcgggg | cttctcgcca | agacctgag | cgttctggcc | 1080 |
| ctgagggaag | gccttggcct | cccgcccggc | gacgaccca | tgctcctcgc | ctacctcctg | 1140 |
| gaccttcca | acaccacccc | cgaggggtg | gcccggcgct | acggcggga | gtggacggag | 1200 |
| gaggcggggg | agcgggccgc | cctttccgag | aggctcttcg | ccaacctgtg | ggggaggctt | 1260 |
| gaggggggag | agaggctcct | ttggctttac | cggaggtgg | agaggcccct | ttccgctgtc | 1320 |
| ctggcccaca | tggaggccac | gggggtgcgc | ctggacgtgg | cctatctcag | ggccttgtcc | 1380 |
| ctggaggtgg | ccgaggagat | cgcccgcctc | gaggccgagt | cttccgcct | ggccggccac | 1440 |
| cccttcaacc | tcaactcccg | ggaccagctg | gaaagggtcc | tctttgacga | gctagggctt | 1500 |
| ccgccatcg | gcaagacgga | gaagaccggc | aagcgctcca | ccagcgccgc | cgtcctggag | 1560 |
| gccctccgcg | aggcccaccc | catcgtggag | aagatcctgc | agtaccggga | gctcaccaag | 1620 |
| ctgaagagca | cctacattga | ccccttgccg | gacctcatcc | accccaggac | gggccgcctc | 1680 |
| cacacccgct | tcaaccagac | ggccacggcc | acgggcaggc | taagtagctc | cgatcccaac | 1740 |
| ctccagaaca | tccccgtccg | caccccgctt | gggcagagga | tccgccgggc | cttcatcgcc | 1800 |
| gaggagggt | ggctattggt | ggccctggac | tatagccaga | tagagctcag | ggtgctggcc | 1860 |
| cacctctccg | cgacgagaa | cctgatccgg | gtcttccagg | aggggcggga | catccacacg | 1920 |
| gagaccgcca | gctggatgtt | cggcgtcccc | cgggaggccg | tggaccccct | gatgcgccgg | 1980 |
| gcggccaaga | ccatcaactt | cggggtcctc | tacggcatgt | cggcccaccg | cctctcccag | 2040 |

```
gagctagcca tcccttacga ggaggcccag gccttcattg agcgctactt tcagagcttc    2100
cccaaggtgc gggcctggat tgagaagacc ctggaggagg caggaggcg ggggtacgtg     2160 gagaccctct tcggccgccg ccgctacgtg ccagacctag aggcccgggt gaagagcgtg    2220
cgggaggcgg ccgagcgcat ggccttcaac atgcccgtcc agggcaccgc cgccgacctc    2280
atgaagctgg ctatggtgaa gctcttcccc aggctggagg aaatggggc caggatgctc     2340 cttcaggtcc acgacgagct ggtcctcgag gccccaaaag agagggcgga ggccgtggcc    2400
cggctggcca aggaggtcat ggaggggtg tatcccctgg ccgtgcccct ggaggtggag     2460
gtggggatag ggaggactg gctctccgcc aaggagtga                            2499
```

<210> SEQ ID NO 2
<211> LENGTH: 810
<212> TYPE: PRT
<213> ORGANISM: Thermus aquaticus

<400> SEQUENCE: 2

```
Met Arg Gly Met Leu Pro Leu Phe Glu Pro Lys Gly Arg Val Leu Leu
  1               5                  10                  15

Val Asp Gly His His Leu Ala Tyr Arg Thr Phe His Ala Leu Lys Gly
             20                  25                  30

Leu Thr Thr Ser Arg Gly Glu Pro Val Gln Ala Val Tyr Gly Phe Ala
         35                  40                  45

Lys Ser Leu Leu Lys Ala Leu Lys Glu Asp Gly Asp Ala Val Ile Val
     50                  55                  60

Val Phe Asp Ala Lys Ala Pro Ser Phe Arg His Glu Ala Tyr Gly Gly
 65                  70                  75                  80

Tyr Lys Ala Gly Arg Ala Pro Thr Pro Glu Asp Phe Pro Arg Gln Leu
                 85                  90                  95

Ala Leu Ile Lys Glu Leu Val Asp Leu Gly Leu Ala Arg Leu Glu
            100                 105                 110

Val Pro Gly Tyr Glu Ala Asp Asp Val Leu Ala Ser Leu Ala Lys Lys
        115                 120                 125

Ala Glu Lys Glu Gly Tyr Glu Val Arg Ile Leu Thr Ala Asp Lys Asp
    130                 135                 140

Leu Tyr Gln Leu Leu Ser Asp Arg Ile His Val Leu His Pro Glu Gly
145                 150                 155                 160

Tyr Leu Ile Thr Pro Ala Trp Leu Trp Glu Lys Tyr Gly Leu Arg Pro
                165                 170                 175

Asp Gln Trp Ala Asp Tyr Arg Ala Leu Thr Gly Asp Glu Ser Asp Asn
            180                 185                 190

Leu Pro Gly Val Lys Gly Ile Gly Glu Lys Thr Ala Arg Lys Leu Leu
        195                 200                 205

Glu Glu Trp Gly Ser Leu Glu Ala Leu Leu Lys Asn Leu Asp Arg Leu
    210                 215                 220

Lys Pro Ala Ile Arg Glu Lys Ile Leu Ala His Met Asp Asp Leu Lys
225                 230                 235                 240

Leu Ser Trp Asp Leu Ala Lys Val Arg Thr Asp Leu Pro Leu Glu Val
                245                 250                 255

Asp Phe Ala Lys Arg Arg Glu Pro Asp Arg Glu Arg Leu Arg Ala Phe
            260                 265                 270

Leu Glu Arg Leu Glu Phe Gly Ser Leu Leu His Glu Phe Gly Leu Leu
        275                 280                 285
```

-continued

```
Glu Ser Pro Lys Ala Leu Glu Ala Pro Trp Pro Pro Glu Gly
    290                 295                 300

Ala Phe Val Gly Phe Val Leu Ser Arg Lys Glu Pro Met Trp Ala Asp
305                 310                 315                 320

Leu Leu Ala Leu Ala Ala Arg Gly Gly Arg Val His Arg Ala Pro
                325                 330                 335

Glu Pro Tyr Lys Ala Leu Arg Asp Leu Lys Glu Ala Arg Gly Leu Leu
            340                 345                 350

Ala Lys Asp Leu Ser Val Leu Ala Leu Arg Glu Gly Leu Gly Leu Pro
            355                 360                 365

Pro Gly Asp Asp Pro Met Leu Leu Ala Tyr Leu Leu Asp Pro Ser Asn
            370                 375                 380

Thr Thr Pro Glu Gly Val Ala Arg Arg Tyr Gly Gly Glu Trp Thr Glu
385                 390                 395                 400

Glu Ala Gly Glu Arg Ala Ala Leu Ser Glu Arg Leu Phe Ala Asn Leu
                405                 410                 415

Trp Gly Arg Leu Glu Gly Glu Glu Arg Leu Leu Trp Leu Tyr Arg Glu
            420                 425                 430

Val Glu Arg Pro Leu Ser Ala Val Leu Ala His Met Glu Ala Thr Gly
            435                 440                 445

Val Arg Leu Asp Val Ala Tyr Leu Arg Ala Leu Ser Leu Glu Val Ala
    450                 455                 460

Glu Glu Ile Ala Arg Leu Glu Ala Glu Val Phe Arg Leu Ala Gly His
465                 470                 475                 480

Pro Phe Asn Leu Asn Ser Arg Asp Gln Leu Glu Arg Val Leu Phe Asp
                485                 490                 495

Glu Leu Gly Leu Pro Ala Ile Gly Lys Thr Glu Lys Thr Gly Lys Arg
            500                 505                 510

Ser Thr Ser Ala Ala Val Leu Glu Ala Leu Arg Glu Ala His Pro Ile
            515                 520                 525

Val Glu Lys Ile Leu Gln Tyr Arg Glu Leu Thr Lys Leu Lys Ser Thr
    530                 535                 540

Tyr Ile Asp Pro Leu Pro Asp Leu Ile His Pro Arg Thr Gly Arg Leu
545                 550                 555                 560

His Thr Arg Phe Asn Gln Thr Ala Thr Ala Thr Gly Arg Leu Ser Ser
                565                 570                 575

Ser Asp Pro Asn Leu Gln Asn Ile Pro Val Arg Thr Pro Leu Gly Gln
            580                 585                 590

Arg Ile Arg Arg Ala Phe Ile Ala Glu Glu Gly Trp Leu Leu Val Ala
            595                 600                 605

Leu Asp Tyr Ser Gln Ile Glu Leu Arg Val Leu Ala His Leu Ser Gly
    610                 615                 620

Asp Glu Asn Leu Ile Arg Val Phe Gln Glu Gly Arg Asp Ile His Thr
625                 630                 635                 640

Glu Thr Ala Ser Trp Met Phe Gly Val Pro Arg Glu Ala Val Asp Pro
                645                 650                 655

Leu Met Arg Arg Ala Ala Lys Thr Ile Asn Phe Gly Val Leu Tyr Gly
            660                 665                 670

Met Ser Ala His Arg Leu Ser Gln Glu Leu Ala Ile Pro Tyr Glu Glu
            675                 680                 685

Ala Gln Ala Phe Ile Glu Arg Tyr Phe Gln Ser Phe Pro Lys Val Arg
    690                 695                 700

Ala Trp Ile Glu Lys Thr Leu Glu Glu Gly Arg Arg Arg Gly Tyr Val
```

```
705                 710                 715                 720
Glu Thr Leu Phe Gly Arg Arg Tyr Val Pro Asp Leu Glu Ala Arg
                725                 730                 735

Val Lys Ser Val Arg Glu Ala Ala Glu Arg Met Ala Phe Asn Met Pro
            740                 745                 750

Val Gln Gly Thr Ala Ala Asp Leu Met Lys Leu Ala Met Val Lys Leu
        755                 760                 765

Phe Pro Arg Leu Glu Glu Met Gly Ala Arg Met Leu Leu Gln Val His
    770                 775                 780

Asp Glu Leu Val Leu Glu Ala Pro Lys Glu Arg Ala Glu Ala Val Ala
785                 790                 795                 800

Arg Leu Ala Lys Glu Val Met Glu Gly Val
                805                 810

<210> SEQ ID NO 3
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 3
gtgggctgaa aagctcccga ttat                                          24

<210> SEQ ID NO 4
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 4
attcaaaggg tatctgggct ctgg                                          24

<210> SEQ ID NO 5
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 5
aggtacctgg ctgtcgtcca tgctgtgttt                                    30

<210> SEQ ID NO 6
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 6
gatgatgggg ttgatgcagc agtgcgtcat                                    30

<210> SEQ ID NO 7
<211> LENGTH: 29
<212> TYPE: DNA
<213> ORGANISM: Artificial Sequence
<220> FEATURE:
<223> OTHER INFORMATION: Description of Artificial Sequence: Primer

<400> SEQUENCE: 7
gcagtaccgg gagctcacca agctgaaga                                     29
```

-continued

```
<210> SEQ ID NO 8
<211> LENGTH: 35
<212> TYPE: DNA
<213> ORGANISM: Artificial Sequence
<220> FEATURE:
<223> OTHER INFORMATION: Description of Artificial Sequence: Primer

<400> SEQUENCE: 8
gcgaagctta ctactccttg gcggagagcc agtcc                              35

<210> SEQ ID NO 9
<211> LENGTH: 36
<212> TYPE: DNA
<213> ORGANISM: Artificial Sequence
<220> FEATURE:
<223> OTHER INFORMATION: Description of Artificial Sequence: Primer

<400> SEQUENCE: 9
ggatctcgtc gtgacccatg gcgatgcctg cttgcc                             36
```